(12) United States Patent
Remers et al.

(10) Patent No.: US 6,297,230 B1
(45) Date of Patent: Oct. 2, 2001

(54) CYANOAZIRIDINES FOR TREATING CANCER

(75) Inventors: William A. Remers; Evan M. Hersh; Robert T. Dorr; Bhashyam Iyengar, all of Tucson, AZ (US)

(73) Assignee: Amplimed, Inc., Tucson, AR (US)

( * ) Notice: Subject to any disclaimer, the term of this patent is extended or adjusted under 35 U.S.C. 154(b) by 0 days.

(21) Appl. No.: 09/446,652

(22) PCT Filed: Jun. 26, 1998

(86) PCT No.: PCT/US98/13346

§ 371 Date: Apr. 10, 2000

§ 102(e) Date: Apr. 10, 2000

(87) PCT Pub. No.: WO99/00120

PCT Pub. Date: Jan. 7, 1999

Related U.S. Application Data

(60) Provisional application No. 60/051,037, filed on Jun. 27, 1997.

(51) Int. Cl.[7] ............... A61K 31/396; C07C 255/46; C07D 203/12
(52) U.S. Cl. ............... 514/183; 548/966; 548/967; 558/434
(58) Field of Search ............... 514/183; 548/966, 548/967; 558/434

(56) References Cited

U.S. PATENT DOCUMENTS

| | | | |
|---|---|---|---|
| 4,282,212 | * | 8/1981 | Berger et al. . |
| 4,517,183 | | 5/1985 | Bosies et al. . |

FOREIGN PATENT DOCUMENTS

2727550 A1 * 1/1979 (DE) .

OTHER PUBLICATIONS

Trapenciers et al. Khim. Geterotsikl. Soedin., (1985), vol. 8, pp. 1070–1074.*

* cited by examiner

*Primary Examiner*—Taofiq A. Solola
(74) *Attorney, Agent, or Firm*—Townsend and Townsend and Crew LLP

(57) ABSTRACT

The present invention is directed to novel anti-cancer compounds of the formula.

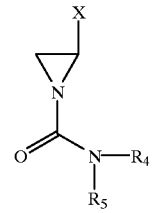

wherein
 X is CN,
 $R_4$ is hydrogen or lower alkyl; and
 $R_5$ is lower alkyl, lower cycloalkyl, alkenyl, alkynyl, aryl, monosubstituted aryl, disubstituted aryl, aryl lower alkyl, lower alkoxycarbonyl lower alkyl, or heterocyclic ring, with the proviso that when X is CN, and $R_4$ is hydrogen, then $R_5$ is not $CH_3$, $C_6H_5$, or, p-nitrophenyl.
 $R_4$, $R_5$ and N taken together form a heterocyclic ring.

13 Claims, 4 Drawing Sheets

CYANOAZIRIDINES FOR TREATING CANCER

CROSS-REFERENCE TO RELATED APPLICATIONS

This application is a 371 of PCT/US98/13346 filed Jun. 26 1998 which claims the benefit of U.S. Provisional Patent Application Ser. No. 60/051,037, filed Jun. 27, 1997.

FEDERALLY SPONSORED RESEARCH AND DEVELOPMENT

Not applicable.

BACKGROUND OF THE INVENTION

1. Field of the Invention

This invention relates to novel cyanoaziridines for treatment of cancer. 2. Description of Related Art This invention is directed towards aziridine-1-carboxamides related to imexon having improved anti-tumor activity.

The search for compounds having anti-tumor activity has included 2-cyanoaziridines with substituents on the nitrogen atom. German patent 2,736,296 (Feb. 22, 1979) claimed 2-cyanoaziridines and its derivatives. German patent 2,727,550 (Jan. 4, 1979) claimed 2-cyanoaziridines with substituted carbonyl, sulfonyl, or phosphoryl groups on nitrogen. East German patent 110 492 (Dec. 20, 1974) claimed 2-cyanoaziridines with alkanoyl and aroyl substituents on nitrogen. It also claimed 2-cyanoaziridine-1-carboxamide. The cyclization of 2-cyanoaziridine-1-carboxamide to imexon, as well as imexon itself, was claimed in U.S. Pat. No. 4,083,987 (Apr. 11, 1978). Two German patents, 2,740,248 (Mar. 15, 1979) and 2,656,323 (Jun. 15, 1978) claimed the preparation of 2-cyano-1-phenoxycarbonylaziridine and its conversion into 2-cyanoaziridine-1-carboxamide. Immunosuppressive activity for imidazolidine derivatives related to imexon was claimed in U.S. Patent 4,996,219.

Imexon (4-imino-1,3-diazabicyclo[3.1.0]hexan-2-one) was developed by Bicker (Immune Modulation and Control of Neoplasia by Adjuvant Therapy, M. A. Ghirigos, Ed., Raven Press, New York, 1978, p. 389) in an investigation of cyanoaziridine derivatives with potential cancerostatic action. It is a cyclic isomer of 2-cyanoaziridine-1-carboxamide, from which it is formed by treatment with a catalytic amount of KOH in methanol as illustrated below (U. Bicker, W. Kampe, and W. Steingross, U.S. Pat. No. 4,083,987, Apr. 11, 1978).

Imexon has both direct cytotoxicity to tumor cells and immunomodulatory effects. It is active against a variety of human tumor cell lines in culture and against fresh human tumor cell lines in clonogenic assay. It is selectively cytotoxic to multiple myeloma in the clonogenic assay (S. E. Salmon and E. M. Hersh, J. Natl. Cancer Inst., 86, 228, 1994). Imexon is active against a variety of transplanted tumors in rodents (U. Bicker and G. Hebold, IRCS Med. Sci.: Cancer; Hematology; Immunology and Allergy; Pharmacology, 5, 428, 1977; U. Bicker and P. Fuhse, Exp. Path. Bd. 10, S. 279–284, 1975) and it is active against human lymphoma, melanoma, and prostate cancer cell lines in SCID mice (Hersh, et al., Proc. Am. Assoc. Cancer Res., 36, 294, 1995). Objective responses were observed in dogs with mast cell tumors after treatment with imexon (R. T. Dorr, J. D. Liddil, M. K. Klein, and E. M. Hersh, Invest. New Drugs, 13, 113, 1995). Despite the presence of an aziridine ring, imexon is not myelosuppressive, which makes it potentially valuable in combination chemotherapy.

SUMMARY OF THE INVENTION

The present invention is directed to novel anti-cancer compounds of the formula:

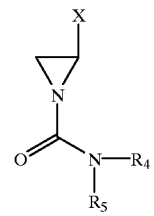

Formula I wherein

X is CN, $CO_2R_1$, or $CONR_2R_3$:

$R_1$ is lower alkyl, cycloalkyl, alkenyl, or aryl lower alkyl;

$R_2$ is hydrogen or lower alkyl;

$R_3$ is hydrogen lower alkyl, lower cycloalkyl, alkenyl, alkynyl, aryl, or heterocyclic ring;

$R_2$, $R_3$ and N taken together form a heterocyclic ring $R_4$ is hydrogen or lower alkyl; and $R_5$ is lower alkyl, lower cycloalkyl, alkenyl, alkynyl, aryl, monosubstituted aryl, disubstituted aryl, aryl lower alkyl, lower alkoxycarbonyl lower alkyl, or heterocyclic ring, with the proviso that when X is CN, and $R_4$ is hydrogen, then $R_5$ is not $CH_3$, $C_6H_5$, or, p-nitrophenyl.

$R_4$, $R_5$ and N taken together form a heterocyclic ring.

In particular, the invention is also directed to compound of the formula 1:

wherein X is CN, $CO_2R_1$ or $CONR_2R_3$ where $R_1$ is an alkyl of 1–6 carbons, a cycloalkyl of 4–7 carbons, alkenyl of 3–6 carbons or a lower alkyl substituted aryl of 7–12 carbons;

$R_2$ is hydrogen or lower alkyl of 1–4 carbons, and $R_3$ is lower alkyl of 1–4 carbons, lower cycloalkyl of 4–7 carbons, alkenyl of 3–6 carbons, an aryl of 4–10 carbons, a substituted aryl of 4–12 carbons or heterocyclic ring of 4–16 ring members;

wherein $R_4$ is hydrogen or lower alkyl of 1–4 carbons; and, wherein $R_5$ is an alkyl of 1–8 carbons, lower cycloalkyl of 4–7 carbons, alkenyl of 3–6 carbons, an aryl of 4–10 carbons, a substituted aryl of 4–12 carbons, a heterocyclic group of 4–16 members and where $R_4R_5$ and N taken together form a heterocyclic ring of between 4 and 16 members.

The invention further includes compound of the formula 1:

wherein X is CN, $CO_2R_1$ or $CONR_2R_3$ where $R_1$ is an alkyl of 1–6 carbons, a cycoaklyl of 4–7 carbons, alkenyl of 3–6 carbons or an lower alkyl substituted aryl of 7–12 carbons;

where $R_2$ is hydrogen or lower alkyl of 1–4 carbons, and where $R_3$ is a lower alkyl of 1–4 carbons, a lower cycloalkyl of 4–7 carbons, an alkenyl, an aryl of 4–10 carbons, a heterocyclic ring of 4–16 members or a substituted aryl or substituted heterocyclic ring where said substitutents are 1 or 2 and independently selected from the group consisting of lower alkyl of 1–4 carbons, nitro, halo substituted lower alkyls of 1–4 carbons, a lower alkyl substituted acyloxy of 1–5 carbons, a lower alkyl substituted acyl of 1–5 carbons;

wherein $R_4$ is hydrogen or lower alkyl of 1–4 carbons; and, wherein $R_5$ is an alkyl of 1–8 carbons, lower cycloalkyl of 4–7 carbons, alkenyl of 3–6 carbons, an aryl of 4–10 carbons, a substituted aryl of 4–12 carbons having 1–2 substitutents wherein the substituents are independently selected from the group consisting of lower alkyl of 1–4 carbons, nitro, halo substituted lower alkyls of 1–4 carbons, a lower alkyl substituted acyloxy of 1–5 carbons, a lower alkyl substituted acyl of 1–5 carbons, a heterocyclic group of 4–16 members. Substituents $R_4$ and $R_5$ may join to form a heterocyclic ring of 4–16 members.

Preferred compounds include those wherein X is CN. Additional preferred compounds are those where X is CN and $R_4$ is hydrogen; and $R_5$ is a straight chain alkyl of 1 to 8 carbons, an unsubstituted aryl, a mono-substituted or disubstituted aryl wherein the aryl is independently substituted with halo, lower alkyl, halo substituted lower alkyl, lower alkyl-substituted acyloxy or lower alkyl-substituted acyloxy.

Also preferred are those compounds wherein X is CN and $R_4$ is hydrogen; and $R_5$ is a heterocyclic group or an unsubstituted aryl. Particularly preferred are those compounds where X is CN and $R_4$ is hydrogen; and $R_5$ is a pyridyl, a phenyl or a naphthyl.

This invention also includes the use of the above identified compounds to treat a variety of cancers by administering to a patient in need of treatment a unit dose of the compounds described above wherein said unit dose is effective to reduce at least one of the symptoms of the cancer. Preferred dose ranges are unit doses of 0.25 to 2 grams. The preferred route of administration is parental.

Specific cancers include multiple myeloma, a B-lymphocyte plasmacytoma including advanced disease refractory to alkylating agent and glucocorticosteroids, advanced stage ovarian epithelial cell cancer, including patients previously treated with alkylating agents, taxanes or platinum-containing anticancer agents, surgically unresectable (metastatic) melanoma in combination with myelosuppressive anticancer agents, multidrug-resistant leukemias of lymphoid and nonlymphoid origin including multidrug-resistant lymphomas and those lymphomas occurring in patients infected with human immunodeficiency virus-1 (AIDS), advanced stage and especially metastatic colon cancer, including those refractory to fluoropyrimidines such as 5-fluorouracil, prostate cancer, advanced stage breast cancers previously treated with alkylating agents, or natural products which induce multidrug resistance (such as doxorubicin, paclitaxel and vincristine) and metastatic lung cancers of small cell and non-small cell types which are not responsive to local radiotherapy or systemic chemotherapy with cytotoxic drugs.

In addition to novel compositions, this invention includes pharmaceutical formulations of the above identified compounds comprising a unit dose of the compounds in a sterile aqueous solution in amounts facilitating the methods of this invention requiring specific modes of administration such as intravenous administration. It is preferred that the compositions also include pharmaceutically acceptable excipients.

DETAILED DESCRIPTION

A. Introduction

Figure 1:
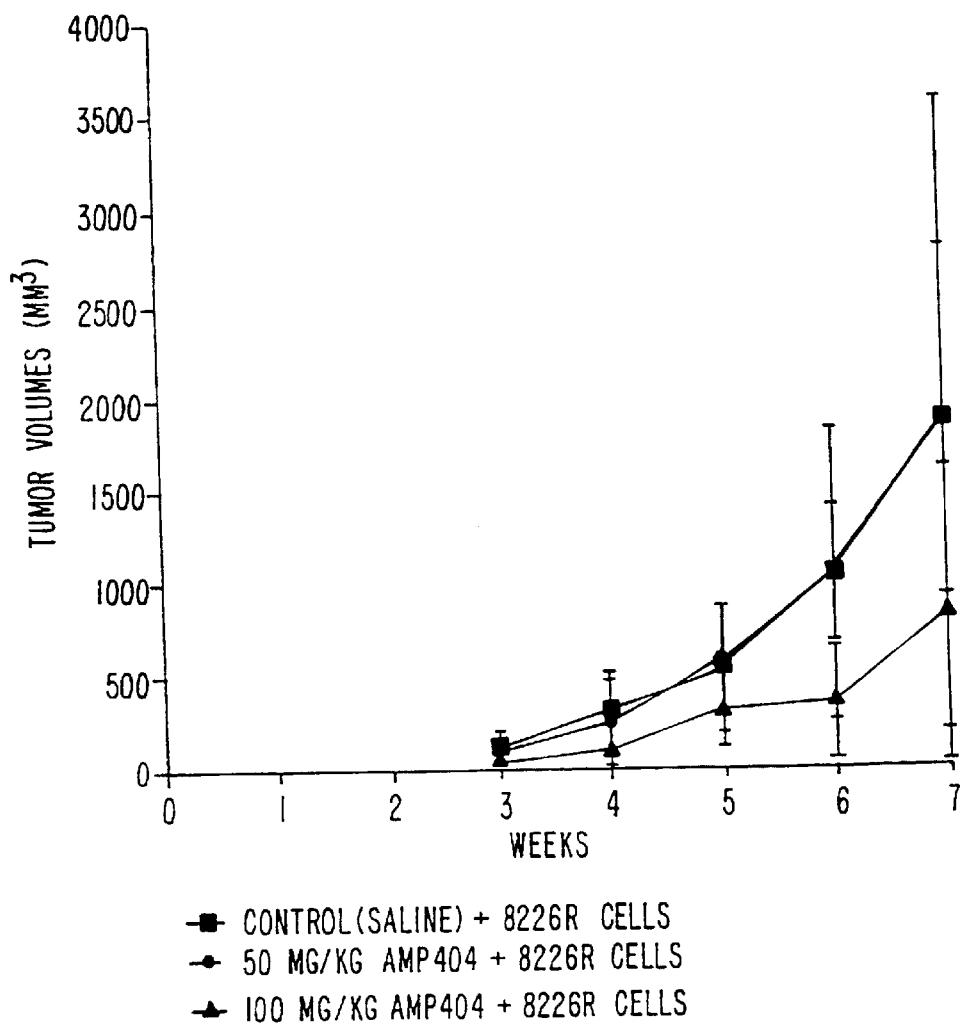
FIG. 1. Median tumor volumes in SCID mice treated with AMP 404.

Imexon has both direct cytotoxicity to tumor cells and immunostimulatory effects. In Phase I human clinical trials conducted in Europe in 1985, it was well tolerated and produced objective responses or stabilized neoplastic diseases in cancer patients. (Sagaster et al: *J Natl Cancer Inst* 87:935, 1995.)

The novel cyanoaziridines of the present invention are improvements on imexon. The novel compounds demonstrate enhanced antitumor potency (>40% decrease in $IC_{50}$) and there is lack of significant cross-resistance with imexon for many of the compounds. Furthermore, there are compounds roughly equal in potency to imexon, that have no significant cross-resistance in an imexon-resistant, human myeloma cell line.

The substituted derivatives of 2-cyanoaziridine have a unique mechanism of action which involves covalent binding to the sulfhydryl moieties found in a number of important cellular thiols. Studies using HPLC/Mass spectrometry have identified covalent attachment of the cyanoaziridine compounds (Molecular ion in positive mode) to the sulfur atoms on the amino acid cysteine ($MH^+$=234) and the main cellular thiol, glutathione (GSH), ($MH^+$=420). In 8226 human multiple myeloma cells. The covalent attachment occurs at the carbon of the ring-opened aziridine moiety in the cyanoaziridines. Furthermore, these cyanoaziridine drugs have been shown to deplete cysteine and GSH levels in 8226 cells direct proportion to their ability to impair cell growth. Thus, analogs with high growth-inhibitory potency also have high potency for reducing the concentrations of both cysteine ($R^2$=0.984) and GSH ($R^2$=0.984) by Pearson product-moment correlation coefficient analyses.

As a consequence of depleting cellular thiols such as cysteine and GSH, tumor cells become highly susceptible to oxidation following exposure to cyanoaziridines. This has been documented in 8226 myeloma cells exposed to cyanoaziridines which develop high levels of peroxides such as hydrogen peroxide, and display a compensatory increase in the enzyme, GSH-peroxidase, which normally detoxifies cellular peroxides using reduced GSH. In addition, cells exposed to cyanoaziridines undergo a form of cell death known as apoptosis, or programmed cell death. This is compatible with an increase in cellular oxidants which are known to be powerful inducers of apoptosis. Human 8226 cells exposed to cyanoaziridines develop characteristic lesions of apoptosis including DNA strand breaks and also display a characteristic morphology. Tumors which rely on intracellular thiols, such as cysteine and GSH for normal growth are especially sensitive to this group of antitumor agents. This includes B-cell lymphocyte-derived tumors such as multiple myeloma as well as several type of non-hematologic (solid) tumors such as lung cancer, and malignant melanoma. Thus, the sequence of events for cell killing with the cyanoaziridines involves (1) depletion of thiols by binding to critical sulfur atoms in amino acids, peptides and proteins, (2) a buildup of organic oxidants including peroxides, and (3) induction of the apoptotic form of cell death.

There are no existing anticancer agents which deplete cellular thiols. Furthermore, there are relatively few agents which are non-myelosuppressive (do not damage the bone marrow) as has been demonstrated for the cyanoaziridine-based agents.

B. Definitions

As used herein, the term "alkyl" when used alone or in combination, consists of a carbon chain containing from one to eight carbon atoms. The alkyl groups may be a straight chain or a branched chain. It includes such groups as methyl, ethyl, propyl, isopropyl, n-butyl, sec-butyl, isobutyl, t-butyl, n-pentyl, amyl, n-hexyl, and the like. The preferred alkyl groups are methyl and ethyl. Lower alkyls are C1–4 and higher alkyls are $C_5$–$C_8$.

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, napthyl, biphenyl, diphenylmethyl and benzophenone among others. The term "aryl" encompasses "arylalkyl."

The term "arylalkyl" is used herein to refer to a subset of "aryl" in which the aryl group is attached to the nucleus shown in Formula 1 by an alkyl group as defined herein.

"Substituted aryl" refers to aryl as just described including one or more functional groups such as lower alkyl, acyl, halogen, alkylhalos (e.g., $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus shown in Formula 1 by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group—OH.

The term "amino" is used to describe primary amines, R—$NH_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

As used herein, the term "acylamino" describes substituents of the general formula RC(O)NR', wherein R' is a lower alkyl group and R represents the nucleus shown in Formula 1 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e., RC(O)OR' or R'OC(O)R, respectively, wherein R comprises the portion of the ester attached either directly or through an intermediate hydrocarbon chain to the nucleus shown in claim 1).

As used herein, the term "aryloxy" denotes aromatic groups which are linked to the nucleus shown in Formula 1 directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in Formula 1. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures.

The term "unsaturated cyclic hydrocarbon" is used to describe a monovalent non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to the nucleus shown in Formula 1.

"Substituted heteroaryl" refers to heteroaryl as just described wherein the heteroaryl nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus shown in Formula 1.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc. It is preferred that the heterocyclic ring contain 5 or 6 ring atoms.

The term "heterocyclicalkyl" defines a subset of "heterocyclic" wherein an alkyl group, as defined herein, links the heterocyclic group to the nucleus shown in Formula 1.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

"Alkylene" refers herein to a divalent lower alkyl substituent as defined above, such as methylene (—$CH_2$—), ethylene (—$CH_2CH_2$—) or propylene (—$CH_2CH_2CH_2$—). "Substituted alkylene" refers to alkylene as just described including one or more functional groups such as lower alkyl, aryl, aralkyl, acyl, halogen, hydroxyl, amino, acylamino, acyloxy, alkoxyl, mercapto and the like.

"Alkenylene" refers herein to a divalent lower alkyl substituent having one or more double bonds, such as ethenylene (—CH=CH—). "Alkynylene" refers herein to a divalent lower alkyl substituent having one or more triple bonds, such as ethynylene (—C≡C—). "Substituted alkenylene" and "substituted alkynylene" refer to an alkenylene or an alkynylene as just described including one or more functional groups such as lower alkyl, aryl, aralkyl, acyl, halogen, hydroxyl, amino, acylamino, acyloxy, alkoxyl, mercapto and the like.

Unless otherwise stated: (i) all numerical ranges are inclusive, i.e., 1–3 or 1 to 3 carbons includes 1,2 and 3 carbons; (ii) heterocyclical substituents may be attached through any available hydrogen that would exist in the non-radical form of the heterocycle member.

C. Synthesizing Imexon Related Cyanoaziridines

The basic nucleus of Formula II, wherein X is CN can be made in accordance with the method of Jänisch, et al. (Jänisch, et al., *Synthesis* 1992, 1211–1212, 1992.) Briefly, 2,3-dibromopropionitrile is treated at 5–15° C. with ammonia and then triethanolamine is added and the mixture is heated at reflux temperature. Following workup, the product is distilled under reduced pressure.

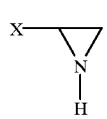

Formula II

When X is $CO_2R_1$, the basic nucleus is made by the method of Kyburz, et al. (Kyburz, et al., *Helv Chim Acta* 49:359–369, 1968.) In this method, esters of 2,3-dibromopropionic acid are stirred with N-phenyl-2-naphthylamine. The ammonia is then evaporated and the product is worked up and distilled under reduced pressure. A variant of this method uses the corresponding esters of 2-bromoacrylic acid in place of the esters of 2,3-dibromopropionic acid. (Kyburz, et al., *Helv Chim Acta* 49:359–369, 1968.)

Compounds containing the basic nucleus wherein X is $CONR_2R_3$ are made by treating methyl or ethyl aziridine-2-carboxylate, prepared as described above, with ammonia or appropriate amines in methanol solution. In the case where $R_2$ and $R_3$ are H, evaporation of solvent gave the product quantitatively according to Kyburz, et al. (Kyburz, et al., *Helv Chim Acta* 49:359–369, 1968). If purification is necessary, the products may be distilled at low pressure (1–10 mm) or recrystallized. Many appropriate amines are commercially available. They include, but are not limited to alkyl (methylamine, etc.), dialkyl (diethylamine, etc.), alkenyl (allylamine), alkynyl (propargylamine), aryl (aniline, etc.), and heterocyclic (pyrrolidine, etc.).

Compounds possessing the basic nucleus can be converted into the compounds of this invention by two different methods. The preferred method depends on the structure of the product and the availability of appropriate isocyanate reagents.

When $R_4$ is H and isocyanates are commercially available or easily prepared, the preferred method is treatment of the basic nucleus with an isocyanate in an inert solvent such as benzene or toluene until complete disappearance of the starting material is indicated by thin-layer chromatography. Generally the product crystallizes when the reaction mixture is cooled. If not, the solvent is removed under reduced pressure to provide the product. Many appropriate isocyanates are commercially available. They include, but are not limited to alkyl (methylisocyanate, etc.), lower cycloalkyl (cyclohexylisocyanate), alkenyl (allylisocyanate), aryl (phenylisocyanate), monosubstituted aryl (tolylisocyanate, etc.), disubstituted aryl (3,4-dichlorophenylisocyanate), aryl lower alkyl (benzylisocyanate), and lower alkoxycarbonyl lower alkyl ($CH_2CO_2C_2H_5$). In other cases, the isocyanate can be prepared from an available intermediate. For example, 3-pyridylisocyanate is made by heating nicotinic acid azide in toluene by the procedure of Hyden and Wilbert. (Hyden, et al., *Chem Ind* (London) 3:1406–1407, 1967.)

When $R_4$ is not H or when an appropriate isocyanate is not available, the preferred method for preparing the compounds of this invention is to first convert the basic nucleus into a carbamate by treating it with 1 to 1.2 equivalents of a chloroformate such as 4-nitrophenyl chloroformate or trichloromethyl chloroformate (reaction 1) in an inert solvent such as benzene, chloroform, or tetrahydrofuran at low temperature (5–20° C.) and removing the solvent under reduced pressure.

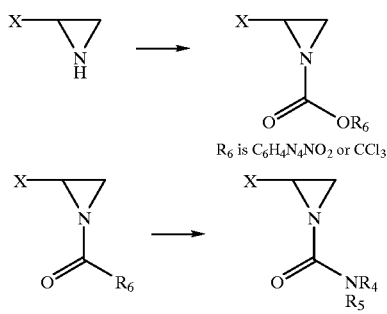

$R_6$ is $C_6H_4N_4NO_2$ or $CCl_3$

The resulting carbamate is treated with appropriate primary or secondary amines to give the desired product (reaction 2). Conditions for conducting this reaction are to treat the carbamate with 1 to 1.2 equivalents of the amine in an inert solvent such as toluene, chloroform, or tetrahydrofuran at room temperature until thin-layer chromatography indicates complete consumption of the carbamate. Many appropriate amines are commercially available. They include, but are not limited to dialkyl (diethylamine, etc.), alkynyl (propargylamine), monosubstituted aryl (2-napthylamine), disubstituted aryl (4-aminobenzoic), aryl lower alkyl (phenethylamine), heterocyclic (piperidine, ect.), and heteroaryl (2-aminothiazole).

The compounds of this invention can be purified by recrystallization from appropriate chemically inert solvents such as toluene, chloroform, and ethyl acetate.

D. Testing Novel Imexon-related Cyanoaziridines for Anticancer Activity

The compounds described above have anticancer activity. A number of biological assays are available to evaluate and to optimize the choice of specific compounds for optimal antitumor activity. These assays can be roughly split into two groups those involving in vitro exposure of agents to tumor cells and in vivo antitumor assays in rodent models and rarely, in larger animals.

The in vitro experiments for new anticancer agents generally involve the use of established tumor cell lines both of animal and, especially of human origin. These cell lines can be obtained from commercial sources such as the American Type Tissue Culture Laboratory in Bethesda, Md. and from tumor banks at research institutions. Exposures to new agents are carried out under simulated physiological conditions of temperature, oxygen and nutrient availability in the laboratory. The endpoints for these in vitro assays can involve: 1) colony formation; 2) a simple quantitation of cell division over time; 3) the uptake of so called "vital" dyes which are excluded from cells with an intact cytoplasmic membrane; or 4) the incorporation of radiolabeled nutrients into a proliferating (viable) cell. Colony forming assays have been used both with established cell lines, as well as fresh tumor biopsies surgically removed from patients with cancer. In this type of assay, cells are typically grown in petri dishes on soft agar, and the number of colonies or groups of cells (>60$\mu$ in size) are counted either visually, or with an automated image analysis system. A comparison is then made to the untreated control cells allowed to develop colonies under identical conditions. Because colony formation is one of the hallmarks of the cancer phenotype only malignant cells will form colonies without adherence to a solid matrix. This can therefore be used as a screening procedure for new agents, and there are a number of publications which show that results obtained in colony forming assays correlates with clinical trial findings with the same drugs.

The enumeration of the total number of cells is a simplistic approach to in vitro testing with either cell lines or fresh tumor biopsies. In this assay, clumps of cells are typically disaggregated into single units which can then be counted either manually on a microscopic grid or using an automated flow system such as either flow cytometry or a Coulter® counter. Control (untreated) cell growth rates are then compared to the treated cell growth rates. Vital dye staining is another one of the older hallmarks of antitumor assays. In this type of approach cells, either untreated or treated with a cancer drug, are subsequently exposed to a dye such as methylene blue, which is normally excluded from intact (viable) cells. The number of cells taking up the dye (dead or dying) are the numerator with a denominator being the number of cells which exclude the dye. These are laborious assays which are not currently used extensively due to the time and the relatively non-specific nature of the endpoint.

In addition to vital dye staining, viability can be assessed using the incorporation of radiolabeled nutrients and/or nucleotides. This is the test method that was used in the Viking Lander to look for life on Mars with the endpoint being how much of a radioactive substance was taken up into a sample as evidence of life activity. In tumor cell assays, a typical experiment involves the incorporation of either ($^3$H) tritium or $^{14}$C-labeled nucleotides such as thymidine. Control (untreated) cells are shown to take up a substantial amount of this normal DNA building block per unit time, and the rate of incorporation is compared to that in the drug treated cells. This is a rapid and easily quantitatable assay that has the additional advantage of working well for cells that may not form large (countable) colonies. Drawbacks include the use of radioisotopes which present handling and disposal concerns.

There are large banks of human and rodent tumor cell lines that are available for these types of assays. The current test system used by the National Cancer Institute uses a bank of over 60 established sensitive and multidrug -resistant human cells lines of a variety of cell subtypes. This typically involves 5–6 established and well-characterized human tumor cells of a particular subtype, such as non-small cell or small cell lung cancer, for testing new agents. Using a graphic analysis system called Compare®, the overall sensitivity in terms of dye uptake (either sulforhodamine B or MTT tetrazolium dye) are utilized. The specific goal of this approach is to identify compounds that are uniquely active in a single histologic subtype of human cancer. In addition, there are a few sublines of human cancer that demonstrate resistance to multiple agents and are known to, in some cases, express the multidrug resistance pump, p-glycoprotein. Assays using these resistant cells are currently underway for screening compounds both from NCI laboratories as well as any submitted from universities or private parties. The endpoint for the NCI assay is the incorporation of a protein dye called sulforhodamine B (for adherent tumor cells) and the reduction of a tetrazolium (blue) dye in active mitochondrial enzymes (for non-adherent, freely-floating types of cells). This latter method is particularly useful for hematologic cancers including myelomas, leukemias and lymphomas.

Generally, once compounds have demonstrated some degree of activity in vitro at inhibiting tumor cell growth, such as colony formation or dye uptake, antitumor efficacy experiments are performed in vivo. Rodent systems are almost exclusively used for initial assays of antitumor activity since tumor growth rates and survival endpoints are well-defined, and since these animals generally reflect the same types of toxicity and drug metabolism patterns as in humans. For this work, syngeneic (same gene line) tumors are typically harvested from donor animals, disaggregated, counted and then injected back into syngeneic (same strain) host mice. Cancer drugs are typically then injected at some later time point(s), either by intraperitoneal, intravenous or oral routes, and tumor growth rates and/or survival are determined, compared to untreated controls. In these assays, growth rates are typically measured for tumors injected growing in the front flank of the animal, wherein perpendicular diameters of tumor width are translated into an estimate of total tumor mass or volume. The time to reach a predetermined mass is then compared to the time required for equal tumor growth in the untreated control animals. Significant findings generally involve a >25% increase in the time to reach the predetermined mass in the treated animals compared to the controls. This is termed tumor growth inhibition. For non-localized tumors such as leukemia, survival can be used as an endpoint and a comparison is made between the treated animals and the untreated or solvent treated controls. In general, a significant increase in life span for a positive new agent is again >20–25% longer life span due to the treatment. Early deaths, those occurring before any of the untreated controls, generally indicate toxicity for a new compound.

For all these assays, the cancer drugs are generally tested at doses very near the lethal dose and 10% ($LD_{10}$) and/or at the determined maximally-tolerated dose, that dose which produces significant toxicity, but no lethality in the same strain of animals and using the same route of administration and schedule of dosing. Similar studies can also be performed in rat tumor models although, because of the larger weight and difficulty handling these animals they are less preferred than the murine models.

More recently, human tumors have been successfully transplanted in a variety of immunologically deficient mouse models. In the initial work, a mouse called the nu/nu or "nude" mouse was used to develop in vivo assays of human tumor growth. In nude mice, which are typically hairless and lack a functional thymus gland, human tumors (millions of cells) are typically injected in the flank and tumor growth occurs slowly thereafter. This visible development of a palpable tumor mass is called a "take". Anticancer drugs are then injected by some route (IV, IM, SQ, PO) distal to the tumor implant site, and growth rates are calculated by perpendicular measures of the widest tumor widths as described earlier. A number of human tumors are known to successfully "take" in the nude rouse model, even though these animals are more susceptible to intercurrent infections due to the underlying immunologic deficiency. An alternative mouse model for this work involves mice with a severe combined immunodeficiency disease (SCID) wherein there is a defect in maturation of lymphocytes. Because of this, SCID mice do not produce functional B- and T-lymphocytes. However, these animals do have normal cytotoxic T-killer cell activity. Nonetheless, SCID mice will "take" a large number of human tumors. Animals with the SCID phenotype are screened for "leakiness" by measuring serum immunoglobulin production which should be minimal to undetectable if the SCID phenotype is maintained. Tumor measurements and drug dosing are generally performed as above. The use of SCID mice has in many cases displaced the nude mouse since SCID mice seem to have a greater ability to take a larger number of human tumors and are more robust in terms of lack of sensitivity to intercurrent infections. Again, positive compounds in the SCID mouse model are those that inhibit tumor growth rate by >20–25% compared to the untreated control.

Testing for drug resistance can involve any of the in vitro and in vivo models, although the in vitro models are better characterized. In these tests, a cell subline is developed for resistance to a particular agent generally by serial exposure to increasing concentrations of the drug either in vitro or rarely in vivo. Once a high degree of resistance is demonstrated (generally >4- to 5-fold) to a particular agent the cell line is further studied for mechanisms of resistance such as the expression of multidrug resistance membrane pumps such as p-glycoprotein or others. These resistant cell lines can then be tested for cross-resistance with other classic anticancer agents to develop a response pattern for a particular cell line. Using this cell line one can then evaluate a new agent for its potential to be active in the resistant cells. This has allowed for the demonstration of both mechanisms of drug resistance, as well as the identification of agents which might have utility in human cancers that have become resistant to existing chemotherapy agents. More recently, the use of resistant human tumor cells has been extended to the SCID mouse model with the development of an in vivo model of multidrug-resistant human multiple myeloma.

All of these test systems are generally combined in a serial order, moving from in vitro to in vivo, to characterize the antitumor activity of a new agent. In general, one wishes to find out what tumor types are particularly sensitive to a new drug and conversely what tumor types are intrinsically resistant to a new agent in vitro. Using this information, experiments are then planned in rodent models to evaluate whether or not the compounds that have shown activity in vitro will be tolerated and active in animals. The initial experiments in animals generally involve toxicity testing to determine a tolerable dose schedule and then using that dose schedule, to evaluate antitumor efficacy as described above. Active compounds from these two types of assays may then be tested in human tumors growing in SCID or nude mice and if activity is confirmed, these drugs then become candidates for potential clinical drug development.

E. Formulating Imexon-related Cyanoaziridines

Various compositions of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of compounds of Formula I.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the drug is employed in treatment. The dosage of the specific compound for treatment depends on many factors that are well known to those skilled in the art. They include for example, the route of administration and the potency of the particular compound. A dosage schedule for humans of from about 0.25 to 2 grams of compound in a single dose, administered parenterally or in the compositions of this invention, are effective for treating different types of cancer.

For parenteral administration, fluid unit dosage forms are prepared utilizing the compounds and a sterile vehicle, 0.9% sodium chloride being preferred. The cyanoaziridine-derivative, depending on the vehicle and concentration used, can be either suspended or dissolved in the vehicle. In preparing solutions the compound can be dissolved in water for injection and filtered sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the cyanoaziridine derivative.

For oral administration, either solid or fluid unit dosage forms can be prepared. For preparing solid compositions such as tablets, the compounds of formula I are mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellullose and the like. Surfactants such as Cremophor EL (polyethoxylated castor oil) or polysorbate 80 (Tween®-80) may also be included.

Additionally, a suppository can be employed to deliver the drug. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 grams.

Implants comprising polymeric devices which slowly release or slowly erode and release within the body to provide continuous supplies of the cyanoaziridine derivative are also of use. Implants include subcutaneous devices such as those routinely used to deliver the hormonal antitumor agent leuprolide or goserelin and other medicaments. Other implants include intratumoral and intraarterial devices.

The implants may be made of polymers which generally comprise but are not limited to non-toxic hydrogels, silicones, polyethylenes, ethylene-vinyl acetate copolymers and other biodegradable polymers. Hydrogels include polyhydroxyalkyl methacrylates, polyacrylamide and polymethacrylamide, polyvinylpyrrolidone and polyvinyl alcohol. A preferred silicone is polydimethylsiloxane. Biodegradable polymers include polylactic acid [PLA], polyglycolic acid [PGA], copolymers of PLA and PGA, and polyamides.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

F. Treatment of Human Cancers with Novel Cyanoaziridines

In general, anticancer therapy is given cyclicly on an every 3 or 4 week basis in order to reduce the tumor load and allow for recovery of normal cells from toxicity. The cyanoaziridine derivative drugs are given by an oral or parenteral route either as a single injection of a large dose or as a series of small daily doses for up to a 4 week period of continuous daily dosing. The continuous dosing regimen may be performed either as a series repeated daily injections, the injection of one large slow release depot formulation (in a subcutaneous or intramuscular site), or the intravenous or intraarterial infusion of agent continuously for several sequential days. Dosing regimens are determined to maximize activity with acceptable, but moderate to severe toxicities. Because the parent cyanoaziridine derivative imexon has not demonstrated myelosuppressive toxicity, it may be possible to continue dosing for prolonged periods with this agent in order to significantly reduce tumor burden and extend survival. These daily injections are given either as a rapid I.V. administration or as a continuous infusion or as an implantation of a slow release formulation in a subcutaneous or intramuscular site.

Measuring Response to Cyanoaziridines

Tumor load is assessed prior to therapy by means of objective scans of the tumor such as with x-ray radiographs, computerized tomography (CAT scans), nuclear magnetic resonance (NMR) scans or direct physical palpation of the tumor mass. Alternatively, the tumor may secrete a marker substance such as alphafetoprotein from colon cancer, CA125 antigen from ovarian cancer, or serum myeloma "M" protein from multiple myeloma. The levels of these secreted products then allow for an estimate of tumor burden to be calculated. These direct and indirect measures of the tumor load are done pretherapy, and are then repeated at intervals following the administration of the drug in order to gauge whether or not an objective response has been obtained. An objective response in cancer therapy generally indicates >50% shrinkage of the measurable tumor disease (a partial response), or complete disappearance of all measurable disease (a complete response). Typically these responses must be maintained for a certain time period, usually one month, to be classified as a true partial or complete response. In addition, there may be stabilization of the rapid growth of a tumor or there may be tumor shrinkage that is <50%, termed a minor response. In general, increased survival is associated with obtaining a complete response to therapy and in some cases, a partial response if maintained for prolonged periods can also contribute to enhanced survival in the patient. Patients receiving chemotherapy are also typically "staged" as to the extent of their disease before and following chemotherapy are then restaged to see if this disease extent has changed. In some situations the tumor may shrink sufficiently and if no metastases are present, then surgical excision may be possible after chemotherapy treatment where it was not possible beforehand due to the widespread disease. In this case the chemotherapy treatment with the novel cyanoaziridine is being used as an adjuvant to potentially curative surgery. In addition, patients may have individual lesions in the spine or elsewhere that produce symptomatic problems such as pain and these may need to have local radiotherapy applied. This may be done in addition to the continued use of the systemic cyanoaziridine.

Assessing Cyanoaziridine Toxicity and Setting Dosing Regimens

Patients are assessed for toxicity with each course of chemotherapy, typically looking at effects on liver function enzymes and renal function enzymes such as creatinine clearance or BUN as well as effects on the t)one marrow, typically a suppression of granulocytes important for fighting infection and/or a suppression of platelets important for hemostasis or stopping blood flow. For such myelosuppressive drugs, the nadir in these normal blood counts, is reached between 1–3 weeks after therapy and recovery then ensues over the next week. Based on the recovery of normal white blood counts, treatments may then be resumed. However, because the cyanoarizidines have not demonstrated serious myelosuppression (bone marrow) toxicity to date, they may be used more frequently in a process called "dose intensification." This indicates the more frequent dosing of a cyanoaziridine agent as a means of achieving more substantial reduction in tumor burden.

In general, complete and partial responses are associated with at least a 1–2 log reduction in the number of tumor cells (a 90–99% effective therapy). Patients with advanced cancer will typically have >$10^9$ tumor cells at diagnosis, multiple treatments will be required in order to reduce tumor burden to a very low state and potentially obtain a cure of the disease.

Using Cyanoaziridines in Combination With Other Agents

Because of the lack of myelotoxicity, the cyanoaziridines may be combined with other existing cytotoxic agents including other drugs which damage the bone marrow. In this regard the cyanoaziridines may offer a distinct advantage over existing agents because they could be combined at full dose with the full dose of bone marrow suppressing drugs due to the lack of myelosuppression for the cyanoaziridines. This has been a major advantage with the use of the nonmyelosuppressive vinca alkaloid, vincristine, in patients with acute leukemia. Similarly, the cyanoaziridines may be combined with a large number of existing myelosuppressive agents in order to provide high dose intensity with multiple agent therapy.

The use of multiple chemotherapy agents is desirable in order to produce a major reduction in tumor load as well as to prevent the emergence of cells resistant to a single therapy.

Clinical Management of Patients Receiving Cyanoaziridines

At the end of a treatment cycle with the cyanoaziridine derivative which could comprise several weeks of continuous drug dosing, patients will be evaluated for response to therapy (complete and partial remissions), toxicity measured by blood work and general well-being classified performance status or quality of life analysis. The latter includes the general activity level of the patient and their ability to do normal daily functions. It has been found to be a strong predictor of response and some anticancer drugs may actually improve performance status and a general sense of well-being without causing a significant tumor shrinkage. The antimetabolite gemcitabine is an example of such a drug that was approved in pancreatic cancer for benefiting quality of life without changing overall survival or producing a high objective response rate. Thus, for some cancers that are not curable, the cyanoaziridines may similarly provide a significant benefit, well-being performance status, etc. without affecting true complete or partial remission of the disease.

In hematologic disorders such as multiple myeloma, lymphoma and leukemia, responses are not assessed via the measurement of tumor diameter since these diseases are widely metastatic throughout the lymphatic and hematogenous areas of the body. Thus, responses to these diffusely disseminated diseases are usually measured in terms of bone marrow biopsy results wherein the number of abnormal tumor cell blasts are quantitated and complete responses are indicated by the lack of detection of any tumor cells in a bone marrow biopsy specimen. With the B-cell neoplasm multiple myeloma a serum marker, the M protein, can be measured by electrophoresis and if substantially decreased this is evidence of the response of the primary tumor. Again, in multiple myeloma, bone marrow biopsies can be used to quantitate the number of abnormal tumor plasma cells present in the specimen. For these diseases generally higher dose therapy is typically used to affect responses in the bone marrow and/or lymphatic compartments.

Administration of Cyanoaziridines

In addition to intravenous (systemic) therapy, with some cancers, drugs may need to be given directly into the central nervous system since they have a low uptake into this compartment. Therefore, the cyanoaziridines may be injected through the intrathecal space between the third and fourth lumbar vertebrae in order to achieve high levels in the cerebral spinal fluid. Alternatively, the drugs may be injected through a subcutaneous sack connected to the brain ventricle (the Ommaya reservoir). In this way the cyanoaziridines can gain access to the central nervous system to reduce tumor cell burden in that compartment. Drugs useful in the central nervous system generally have low sclerosing or vesicant potential; current examples include the antimetabolites cytarabine and methotrexate. The cyanoaziridines also have a low sclerosing and vesicant potential.

Drug Administration

For a typical therapeutic use of imexon to treat a systemic cancer not in the central nervous system the drug is dissolved in a physiologic solution such as 5% dextrose in water (D5W) or 0.9% sodium chloride for injection (normal saline). This solution is then infused intravenously either via a peripheral vein or a central vascular access device at a slow infusion rate of several mL/minute. The infusion may be continued for several days or it may be given in a single daily injection over a period of 30 minutes to 4 hours. Throughout this infusion the patient is monitored for any acute distress such as a hypersensitivity reaction to the drug or a change in blood pressure or mental status. The veins are also monitored to make sure that medication is not leaking out (extravasation). At the conclusion of the infusion the patient may remain under observation for a short time period before returning home or to work.

The range of imexon (analog) doses may vary from 10 mg to 10 grams per day for single or consecutive daily doses. Prolonged daily dosing has been shown to be tolerable and active in tumor-bearing mice and dogs receiving therapy for up to one month. Thus, a "typical" clinical dose schema for humans with cancer would comprise: 1–10 g/day by IV infusion for one up to thirty consecutive days, followed by a "rest period" of 1–2 weeks, for evaluation of response and resolution of any toxicities, which are expected to involve non-cumulative gastrointestinal effects. The rates of infusion are typically 1–500 µg (generally 100–300) per mL per $m^2$ at rates of 1–500 (typically 100–300) mg/hour. These treatment schedules could be continued indefinitely until there is evidence of disease progression or severe toxicity.

Table 1A shows the designation numbers of imexon analogs (AMPs) and their respective chemical formulae. When an AMP designation number is used herein, its chemical formula can be found in Table 1A.

TABLE 1A

AMP designation of imexon analogs and their respective chemical formulae.

| compound | R |
| --- | --- |
| AMP-400 | (imexon) |
| 403 | $CH_3$ |
| 404 | $C_6H_5$ |
| 405 | $COCl_3$ |
| 406 | $C_2H_5$ |
| 407 | o,p-$C_6H_3Cl_2$ |
| 408 | pm,p-$C_6H_3Cl_2$ |
| 409 | H (intermed.) |
| 410 | $C(CH_3)_3$ |
| 412 | $CH_2C_6H_5$ |
| 413 | c-$C_6H_{11}$ |
| 414 | $C_4H_9$ |
| 415 | p-$FC_6H_4$ |
| 416 | p-$CF_3C_6H_4$ |
| 417 | p-$O_2NC_6H_4$ |
| 418 | Bis-cyanoaziridine |
| 419 | p-$C_2H_5OCOC_6H_4$ |
| 420 | $C_2H_5OCOCH_2$ |
| 421 | $C_5H_4N$ (pyr.) |
| 422 | $H_2NSO_2C_6H_4$ |
| 423 | 1-Naphthyl |
| 424 | o-$CH_3CO_2C_6H_4$ |
| 425 | m-$CH_3COC_6H_5$ |

Table 1B below summarizes the projected clinical uses for the imexon analog series. Based on the current preclinical data, the imexon analogs will require parenteral administration by the intramuscular, intravenous or subcutaneous route. A depot (IM or SC) formulation would be especially advantageous to prolong drug levels and reduce injection frequency. The parent compound was not active orally in mice, but select analogs will overcome this limitation due to their enhanced stability in acidic aqueous solutions, and/or by incorporation into an oral formulation which is protected from gastrointestinal degradation (i.e., enteric coatings or other timed-release oral formulations.

TABLE 1B

Clinical Uses of the Imexon Analog Series in Treating Human Cancer.

| Disease | Rationale |
| --- | --- |
| Multiple Myeloma | Activity demonstrated in human tumors in vitro and in vivo (in the SCID mouse model) |
| Lung Cancer, Breast Cancer | Parent compound active in Phase I human clinical trial |
| Malignant Malanoma | Human cells sensitive to analogs in in vitro and parent compound active in Phase I human clinical trial and in vivo in animal AIDS-related lymphoma models |
| AIDS-Related Lymphoma | Parent compound active in vitro Analogs active against lymphoma cells in vitro |
| Multidrug-Resistant (MDR) Tumors (Myeloma, Leukemia Breast and Colon Carcinoma) | Analogs not affected by p-glycoprotein-mediated MDR |
| Prostate Cancer | Parent compound active in human tumors in vivo in the SCID mouse model |

Management of Cyanoaziridine Toxicities and Responses

Based on the in vitro and in vivo observations of enhanced and tumor efficacy for prolonged exposure, a clinical trial design to incorporate this requirement, has been formulated for imexon and imexon-related analogs. Our prior studies of imexon in mice and dogs suggest that the maximally-tolerated human dose will be approximately 500 mg/m²/day. (Note an "average" adult is approximately 1.8 m² in body surface area.)

It is anticipated that the major toxicity with the cyanoaziridines will be acute nausea and vomiting and these will be pretreated with combinations of effective antiemetics. In addition, several weeks after the conclusion of the cyanoaziridine derivative infusions the patients will have blood work drawn to evaluate both toxic effects on different normal tissues including the bone marrow, kidney and liver as well as evidence for reduction in any of the known tumor markers as described earlier. In general the patients are reassessed on a monthly basis and therapy may be then reinstituted if there is no evidence of tumor growth and/or if there is evidence of actual response to the prior therapy as described earlier. These treatments may be combined with other anticancer agents given on a cyclical basis of usually every 2–4 weeks with approximately 5–6 courses typically given in order to comprise a complete trial of chemotherapy. At this time the patient is completely reassessed for response and toxicity and patients may either continue on therapy if there is some evidence of residual disease or they may go into a period of observation if the tumor has been significantly reduced. With any increasing sign of tumor spread patients may go back onto chemotherapy with the cyanoaziridine and/or other agents or a decision may be made to switch to different types of drugs and/or modality such as radiation therapy.

EXAMPLES

The following examples are provided by way of illustration only and not by way of limitation. Those of skill will readily recognize a variety of noncritical parameters which could be changed or modified to yield essentially similar results.

Example 1

2-Cyanoaziridine-1-(N-methyl)carboxamide

To an ice-cold mixture of 2-cyanoaziridine and toluene was added an ice-cold solution of methyl isocyanate (1.05 equivalents) in toluene at a rate to keep the temperature below 5° C. The mixture was stirred for one hour in an ice bath and then placed in a refrigerator overnight. The resulting precipitate was collected, washed with toluene, and dried under vacuum to give a 94% yield of the title compound as a solid with m.p. 98–100° C.: MS (El) 125($M^+$); $^1H$ NMR ($CDCl_3$, TMS) 2.47 (d, 1, J=3 Hz), 2.57 (d, 1, J=6 Hz) 2.8 (d, 3, J=5 Hz), 3.05 (2d, 1, J=Hz, 3 Hz) 6.18 (s, 1, NH).

Example 2

2-Cyanoaziridine-1-(N-ethyl)carboxamide

This compound was prepared from 2-cyanoaziridine and ethylisocyanate in 63% yield by the procedure described in Example 1. It had m.p. 58–62° C.: MS (EI) 139 ($M^+$); $^1H$ NMR ($CDCl_3$, TMS) 1.1 (t, 3, J=6 Hz), 2.4 (d, 1, J=3 Hz), 2.50 (d, 1, J=6 Hz), 2.97 (2d, 1, J=6 Hz, 3 Hz), 3.3 (q, 2, J=6 Hz (s, 1, NH).

Example 3

2-Cyanoaziridine-1-(N-butyl)carboxamide

This compound was prepared from 2-cyanoaziridine and n-butylisocyanate in 92% yield by the procedure described in Example 1. It had m.p. 32–34° C.: $^1H$ NMR ($CDCl_3$, TMS) 1.0 (t, 3), 1.2–1.5 (m, 2), 1.6–2.1 (m, 2), 2.5 (d, 1, J=3 Hz), 2.55 (d, 1, J=6 Hz), 3.19 (2d, 1, J=6 Hz, 3Hz), 3.6 (m, 2), 5.8 (s, 1, NH).

Example 4

2-Cyanoaziridine-1-(N-t-butyl)carboxamide

This compound was prepared from 2-cyanoaziridine and t-butylisocyanate in 81% yield by the procedure described in Example 1. It had m.p. 46–48° C.: $^1$H NMR (DMSO-d$_6$, TMS) 1.4 (s, 9), 2.84 (d, 1, J=3 Hz), 2.86 (d, 1, J=6 Hz), 3.0 (2d, 1, J=6Hz, 3Hz) 5.8 (br. s, NH).

Example 5

2-Cyanoaziridine-1-(N-cyclohexyl)carboxamide

This compound was prepared from 2-cyanoaziridine and cyclohexylisocyanate in 64% yield by the procedure described in Example 1. It had m.p. 98–102° C.: $^1$H NMR (CDCl$_3$, TMS) 1.2–1.5 (m, 5), 1.6–2.1 (m, 5), 2.45 (d, 1,J=3 Hz), 2.53 (d, 1, J=6 Hz), 3.015 (2d, 1, J=6 Hz, 3 Hz), 3.6 (m, 1), 5.8 (s, 1, NH)

Example 6

2-Cyanoaziridine-1-(N-benzyl)carboxamide
Method A

This compound was prepared from 2-cyanoaziridine and benzylisocyanate in 25% yield by the procedure described in Example 1. It had m.p. 42–44° C.: $^1$H NMR (CDCl$_3$, TMS) 2.36 (d, 1, J=3 Hz), 2.46 (d, 1, J=6 Hz), 2.93 (2d, 1, J=6 Hz, 3 Hz), 4.4 (d, 2), 6.8 (s, 1, NH), 7.4 (m,5).
Method B A solution of 175 mg of 2-cyanoaziridine and 0.36 mL of triethylamine in 5 mL of THF was cooled and stirred in an ice bath. A solution of 550 mg of 4-Nitrophenyl chloroformate in 2.5 mL of THF was added at a rate that kept the temperature below 10° C. When the addition was complete, the solution was stirred 2 hours at room temperature and then filtered to remove triethylamine hydrochloride. The filtrate was concentrated under reduced pressure and the residual oil was stirred with 5 mL of toluene for 30 minutes. The pale yellow precipitate that formed was washed with toluene (2×5 mL) and dried under vacuum to afford a 33% yield of 4-nitrophenyl 2-cyanoaziridine-1-carboxylate, m.p. 100–104°C.

A mixture of 4-nitrophenyl 2-cyanoaziridine-1-carboxylate and benzylamine (1:1.1 molar ratio) in THF was stirred vigorously at room temperature. The progress of the reaction was monitored by thin-layer chromatography on silica gel with chloroform-methanol (1:9) as solvent. When the starting materials were consumed (about 2 hours), the solution was concentrated under reduced pressure and the title compound was freed from 4-nitrophenol by washing with THF. This procedure gave the title compound with m.p 42–44° C. and a $^1$H NMR spectrum identical with that of the sample described in Method A.

Example 7

2-Cyanoaziridine-1-[N-(ethoxycarbonyl)methyl] carboxamide

This compound was prepared from 2-cyanoaziridine and ethyl isocyanatoacetate in 50% yield by the procedure described in Example 1, except that it was a colorless oil and did not crystallize on refrigeration. Instead, it was dissolved in cold chloroform and diluted with cold hexane. The mixture was stirred briefly and then the solvent was decanted. The residual title compound had $^1$H NMR (CDCl$_3$, TMS) 1.22 (t, 3, J=7 Hz), 2.49 (d, 1, J=3 Hz), 2.56 (d, 1, J=6 Hz), 3.07 (2d, J=6 Hz, 3 Hz), 3.91 (d, 2), 4.15 (q, 2, J=7 Hz ), 6.74 (t, 1, NH).

Example 8

2-Cyanoaziridine-1-(N-phenyl)carboxamide

This compound was prepared from 2-cyanoaziridine and phenylisocyanate in 71% yield by the procedure described in Example 1. It had m.p. 88–90° C.: MS (El) 187(M$^+$); $^1$H NMR (DMSO-d$_6$, TMS) 2.65 (d, 1, J=3 Hz), 2.69 (d, 1, J=6 Hz), 3.57 (2d, 1, J=6 Hz, 3 Hz), 7.05 (t, 1), 7.45 (d, 2), 7.60 (d, 2), 10.2 (s, 1, NH).

Example 9

2-Cyanoaziridine-1-[N-(4-fluorophenyl)] carboxamide

This compound was prepared from 2-cyanoaziridine and (4-flourophenyl)isocyanate in 54% yield by the procedure described in Example 1. It had m.p. 99–100° C.: $^1$H NMR (DMSO-d$_6$, TMS) 2.55 (d, 1, J=3 Hz), 2.68 (d, 1, J=6 Hz), 3.20 (2d, 1, J=6 Hz, 3 Hz), 7.0 (d, 2, J=9 Hz), 7.5 (d, 2, J=9 10.2 (s,1, NH).

Example 10

2-Cyanoaziridine-1-[N-(4-trifluorophenyl)] carboxamide

This compound was prepared from 2-cyanoaziridine and 4-(trifluorophenyl)isocyanate in 91% yield by the procedure described in Example 1. It had m.p. 166–168° C.: $^1$H NMR (DMSO-d$_6$, TMS) 2.62 (d, 1, J=3 Hz), 2.74 (d, 1, J=6 Hz), 3.32 (2d, 1, J=6 Hz, 3 Hz), 7.54 (d, 2, J=9 Hz), 7.74 (d, 2, J=9 Hz), 10.2 (s, 1, NH).

Example 11

2-Cyanoaziridine-1-[N-(4-nitrophenyl)]carboxamide

This compound was prepared from 2-cyanoaziridine and 4-(nitrophenyl)isocyanate in 89% yield by the procedure described in Example 1. It decomposed above 230° C.: $^1$H NMR (DMSO-d$_6$, TMS) 2.77 (d, 1, J=3 Hz), 2.81 (d, 1, J=6 Hz), 3.69 (2d, 1, J=6 Hz, 3 Hz), 7.8 (d, 2, J=9 Hz), 8.2(d, 2, J–9 Hz), 10.8 (s, 1, NH).

Example 12

2-Cyanoaziridine-1-[N-(2,4-dichlorophenyl)] carboxamide

This compound was prepared from 2-cyanoaziridine and (2,4-dichlorophenyl)isocyanate in 50% yield by the procedure described in Example 1. It had m.p. 110–114° C.: $^1$H NMR (DMSO-d$_6$, TMS) 2.70 (d, 1, J=3 Hz), 2.71 (d, 1, J=6 Hz), 3.57 (2d, 1, J=6 Hz, 3 Hz), 7.4 (d, 1, J=6 Hz), 7.6 (d, 1, J=6 Hz), 7.7 )s, 1) 10.0 (s, 1, NH).

Example 13

2-Cyanoaziridine-1-[N-(3,4-dichlorophenyl)] carboxamide

This compound was prepared from 2-cyanoaziridine and (3,4-dichlorophenyl)isocyanate in 76% yield by the procedure described in Example 1. It had m.p. 132–134° C.: $^1$H NMR (DMSO-d$_6$, TMS) 2.71 (d, 1, J=3 Hz), 2.73 (d, 1, J=6 Hz), 3.62 (2d, 1, J=6Hz, 3 Hz), 7.5 (2d, 1, J=9 Hz, 3 Hz), 7.6 (d, 1, J=9Hz), 7.9 1, J=3 Hz), 10.6 (s, 1, NH).

Example 14

2-Cyanoaziridine-1-[N-(4-ethoxycarbonylphenyl)] carboxamide

This compound was prepared from 2-cyanoaziridine and ethyl 4-isocyanatobenzoate in 90% yield by the procedure described in Example 1. It had m.p. 162–165° C.: $^1$H NMR (DMSO-d$_6$, TMS) 1.3 (t, 3, J=6 Hz), :2.72(d, 1, J=3 Hz 2.76 (d, 1, J=6 Hz), 3.64 (2d, 1, J=6 Hz, 3 Hz), 4.3 (q, 2, J=6 Hz), (7.69 (d, 2, J=9 Hz), 7.73 (d, 2, J=9 Hz), 10.63 (s, 1, NH).

Example 15

2-Cyanoaziridine-1-[N-(3-acetylphenyl)] carboxamide

This compound was prepared from 2-cyanoaziridine and (3-acetylphenyl)isocyanate in 74% yield by the procedure described in Example 1. It had m.p. 110–112° C.: $^1$H NMR (DMSO-d$_6$, TMS) 2.6(s, 3), 2.71 (d, 1, J=3 Hz), 2.74 (d, 1, J=6 Hz), 3.63 (2d, 1, J=6 Hz, 3 Hz), 7.5 (t, 1, J=9 Hz), 7.7 (d, 1, J=9Hz), 7.85 (d, 1, J=9 Hz), 8.1 (s, 1), 10.5 (s, 1, NH).

Example 16

2-Cyanoaziridine-1-[N-(2-acetoxyphenyl)] carboxamide

This compound was prepared from 2-cyanoaziridine and (2-acetoxyphenyl)isocyanate in 10% yield by the procedure described in Example 1. It had m.p. 100–102° C.: $^1$H NMR (CDCl$_3$, TMS) 2.38 (s, 3), 2.55 (br. s, 1), 2.64 (br. s, 1, ), 3.20 (br. s, 1), 7.15 (br. s, 2), 7.2–7.6 (br. s, 1), 7.68 (br. s, 1), 7.96 (s, 1, NH). In this spectrum, the expected doublets were not resolved, but appeared as broad singlets.

2-Acetylbenzoic acid azide was prepared by reacting 2-acetoxybenzoyl chloride with sodium azide in acetone and water at 0–5° C. for 24 hours. It had an IR peak at 2245 cm$^{-1}$ (azide). The crude azide was then heated in benzene at 70–75° C. under nitrogen for 2 hours to give 2-acetoxyphenylisocyanate.

Example 17

2-Cyanoaziridine-1-[N-(4-sulfamylphenyl)] carboxamide

2-Cyanoaziridine-1-[N-(4-chlorosulfonyl)]carboxamide was prepared from 2-cyanoaziridine and (4-chlorosulfonylpheny)isocyanate by the procedure described in Example 1. It had m.p. 142–144° C. Without further purification, it was converted by treatment with liquid ammonia into the title compound, in overall yield of 39%: m.p. 170–174° C.; $^1$H NMR (DMSO-d$_6$, TMS) 2.72 (d, 1, J=3 Hz), 2.74 (d, 1, J=6 Hz), 3.7 (2d, 1, J=6 Hz, 3 Hz), 7.26 (s, 2, SO$_2$NH$_2$), 7.69 (d, 2), 7.73 (d, 2) 10.6 (s, 1, CONH$_2$).

Example 18

2-Cyanoaziridine-1-[N-(1-naphthyl)]carboxamide

This compound was prepared from 2-cyanoaziridine and 1-naphthylisocyanate in 56% yield by the procedure described in Example 1. It had m.p. 98–100° C.: $^1$H NMR (CDCl$_3$, TMS) 2.6 (br. s, 1), 2.7 (br. s, 1), 3.2 (br. s, 1), 7.4 (br. s, 1), 7.5 (m, 2), 7.7 (br. s, 2), 7.8 (br. s, 2), 8.1 (s, 1, NH).

In this spectrum, the expected doublets were not resolved and appeared as broad singlets.

Example 19

2-Cyanoaziridine-1-[N-(3-pyridyl)]carboxamide

This compound was prepared from 2-cyanoaziridine and 3-pyridylisocyanate by the procedure described in Example 1, except that the solvent was benzene. It had m.p. 205° C. (dec.): $^1$H NMR (DMSO-d$_6$, TMS) 2.72 (d, 1, J=3 Hz), 2.76 (d, 1, J=6 Hz), 3.65 (2d, 1, J=6 Hz, 3Hz), 7.36 (d, 1), 7.97 (d, 1), 8.27 (d, 1), 8.71 (s, 1, NH), 10.5 (br. 2, 1, NH).

3-Pyridylisocyanate was prepared from nicotinic acid hydrazide by way of nicotinic acid azide following the literature procedure. (Hyden, et al., *Chem Ind* (London) 3:1406–1407, 1967.) It had an IR peak at 2250 cm$^{-1}$ (isocyanate). The overall yield of the title compound was 10%.

Example 20

In vitro and in vivo model systems for testing the compounds of this invention.

The compounds of the present invention were tested for antitumor activity in various model systems. These systems included the following:

1) in vitro tumor cell viability assays using MTT and SRB dye reaction endpoints.
2) in vivo survival studies in mice with severe combined immunodeficiency disease (SCID) bearing solid flank tumors.

Sulforhodamine B (SRB) Assay for Adherent Tumor Cells

Background

Sulforhodamine B (SRB) is a protein binding aminoxanthene dye with two sulfonic acid groups. (Lillie, R. D., *H. J. Conn's Biological Stains,* 9th Ed., Baltimore; Williams & Wilkins, 1977.) It quantitates whole cell protein content by the intensity of dye staining and relates this to the number of viable cells. This assay assumes that dead cells either lyse, are removed during the procedure, or otherwise do not contribute to the colorimetric endpoint. The SRB assay is used for cells which normally adhere to surfaces (in this case plastic culture flasks or petri dishes) as part of their requirement for growth and division in vitro. The SRB assay is currently used by the National Cancer Institute in the anticancer drug screening program. (Skehan, et al., *J Natl Cancer Inst* 82:1107–1112, 1990; Rubinstein, et al., *J Natl Cancer Inst* 82:1113–1118, 1990.) Methodologic comparisons have shown that SRB results are linear for the number of tumor cells over a 100-fold range, and for protein content determined by a modified Lowry method or Standard Bradford (Bradford, M., *Anal Biochem* 72:248–254, 1976) methods. The visible pink colorimetric endpoint is also indefinitely stable and is more sensitive for quantitating cell numbers than the Lowry or Bradford colorimetric methods and is comparable in sensitivity to fluorescent detection methods. (Lillie, R. D., H. J. Conn's *Biological Stains,* 9th Ed., Baltimore; Williams & Wilkins, 1977.)

Methodology

Cell cultures of $10^3$–$10^7$ cells growing in 96-well plastic microtiter plates are fixed with 50% trichloroacetic acid (TCA) for 30 minutes at 4° C. The cells are then stained with 0.4% (w/v) sulforhodamine B (SRB) dissolved in 1% acetic acid. Unbound dye is removed by 4 washes with 1% acetic acid, and protein-bound dye is extracted with 10 mM unbuffered Tris® base [tris(hydroxymethyl)aminomethane]. The optical density (OD) of this extracted solution is measured at 564 nM in a microtiter plate ultraviolet absorbance detector. Cell viability is expressed as percent of control by dividing the optical densities and multiplying the result by 100.

Microculture Tetrazolium (MTT) Assay for Tumor Cells

Tumors are disaggregated into single cell suspensions using mechanical, hypoosmotic, and/or enzymatic (trypsin) methods. The cells are plated at a concentration of $3-5 \times 10^4$ per 1 mL well into plastic 96-well plates. Growth medium containing 5–10% (vol/vol) heat-inactivated fetal bovine serum and penicillin/streptomycin (both 100 mg/mL) are added prior to incubation at 37° C. for 6 days. Afterwards the medium containing the drug is removed, the cells are centrifuged in fresh medium or phosphate-buffered saline (pH 7.4). A tetrazolium dye, (3,4,5-dimethylthiazol-2-yl)-2, 5-diphenyl tetrazolium (MTT), is then added. (Mossman, T., *J Immunol* 65:55–63, 1983.) This dye forms a colored formazan product upon activation by mitochondrial reductases in viable cells. Typically, the formazan product is solubilized in acid-propanol or DMSO. The intensity of the color is proportional to viable cell numbers and this is quantitated by spectrophotometric absorbance at 570 nM on a micro ELISA plate reader. The results are calibrated in % control absorbance from untreated tumor cells. (Alley, et al., *Cancer Res* 48:589–601, 1988.)

Testing for Antitumor Efficacy in Mice with Severe Combined Immunodeficiency Disease (SCID)

Background

The SCID mouse represents an autosomal recessive mutation in an inbred strain of $C_1B$-17 mice which renders the animals profoundly immunodeficient and able to accept tissue xenografts from rats, humans or other strains of mice. (Ware, et al., *J Immunol Methods* 85:353–361, 1985.) The immunologic defect results from an inability to carry out normal immunoglobulin and T-cell receptor recombination reactions during the development of T- and B-lymphocytes. This renders mice with very low levels of T- and B-cells, and low levels of antibody production which allows foreign (allogeneic or xenogeneic) tissue grafts to grow in vivo. A variety of human tumor tissue types have been shown to grow into palpable tumors following subcutaneous injection into SCID mice. (Phillips, et al., *Curr Top Microbiol Immunol* 152:259–263, 1989.) Compared to athymic nude mice, SCID mice accept more tumor tissue types and breed more efficiently. (Phillips, et al., *Curr Top Microbiol Immunol* 152:259–263, 1989.) The SCID mice are also more sensitive to ionizing radiation (Budach, et al., *Cancer Res* 52(22):6292–6296, 1992) due to a defect in DNA double strand break repair. (Chang, et al., *Cancer Res* 53:1244–1248, 1993.) Because some SCID mice can spontaneously revert to a more normal phenotype, serum immunoglobulin C (IgG) levels are routinely measured and if elevated (leaky phenotype syndrome), the mouse is excluded from further study.

Methodology

The SCID mouse colony is maintained in a barrier facility with specially filtered air, autoclaved (sterilized) food and water and protective handling precautions (gloves, mask, gown) to prevent inadvertent infection. For tumor studies, human tumor cells are grown in vitro, harvested, counted and injected subcutaneously into the front flank area. Tumor cell innocula range from $10^6-2 \times 10^7$ cells/mouse. Palpable tumors begin to develop after 1–3 weeks and sizes are determined by caliper measure of the widest perpendicular diameters. These dimensions are converted to mass using the formula:

$$(L \times W^2) \div 2$$

wherein W=the shorter of the two dimensions and L=the longer diameter value.

Tumor growth rates are plotted as mass (g) per days after inoculation.

Drug treatments are given by intravenous (IV) or intraperitoneal (IP) injection beginning 24 hours after tumor implantation (day 1). For imexon analog 404 studies, $20 \times 10^6$ 8226 myeloma cells exhibiting 40-fold resistance to doxorubicin (8226) (Dalton, et al., *Cancer Res* 46:5125–5130, 1986) were injected in SCID mice (5/group) on day 0. Drug therapy began 1 day later with AMP-404 dissolved in a water-miscible co-solvent system containing (per mL): benzyl alcohol 30 mg; polysorbate 80 mw, 80 mg; polyethylene glycol 300 mw, 650 mg; and q.s. to 1.0 mL in absolute ethanol. The daily dose was either 50 mg/kg or 100 mg/kg. Therapy was continued daily for 4 weeks and tumors were measured three times per week up to the 7 week ending period (two weeks after stopping drug therapy).

Results with AMP-404 in SCID Mice Bearing Human 8,226 Myeloma Tumors

Daily treatment with AMP-404 100 mg/kg resulted in a reduced rate of tumor growth. This was statistically significant at 3 weeks. At the end of the 6 week experiment, mean control tumor size was approximately 1,000 mm$^3$ in the control group and in the group treated with 100 mg/kg it was approximately 300 mm$^3$ (Table 2). This group also experienced a mean body weight loss of 15–20% compared to the control group. There was no apparent weight loss or antitumor effect in the group of SCID mice treated with 50 mg/kg of AMP-404. The tumor take rate (% of inoculated mice developing palpable tumors) was 100% in all 3 groups. The onset of developing palpable tumors was 3 weeks after inoculation. The results are provided in FIG. 1. These results show that AMP-404 is active against multidrug-resistant human myeloma cells in vivo. Antitumor effects at the 100 mg/kg dose were associated with a mean 50% reduction in tumor volume. There was no drug-induced lethality, but this regimen did reduce total body weight by 15–20%. The lower AMP-404 dose of 50 mg/kg was not active.

TABLE 2

Effect of AMP-404 on Human 8226 Myeloma Tumor Growth in SCID Mice

| Group (Dose) | No. Mice | Mean (SD) Tumor Volume in mm³ | | | | |
|---|---|---|---|---|---|---|
| | | Week 3 | Week 4 | Week 5 | Week 6 | Week 7 |
| Control (Solvent) | 5 | 109.6 (37.9) | 311.9 (204.3) | 530.4 (339.6) | 1,042.1 (794.1) | 1,891 (1,692.3) |
| AMP-404 (50 mg/kg) | 5 | 104.2 (78.6) | 247.9 (225.9) | 574.2 (296.2) | 1,020 (396.2) | 1,858.4 (941.4) |
| AMP-404 (100 mg/kg) (P-value)* | 5 | 32.9 (17.9)* | 104.9 (81.8) | 312.5 (195.5) | 357.3 (314.5) | 824.5 (793.7) |
| (P-Value)* | | (.005) | (.068) | (.229) | (.100) | (0.19) |

*Unpaired T-test compared to control group.

Results with Aziridine-1-carboxamides in Tumor Cell Lines In Vitro

Table 3 gives the potencies of the new aziridine-1-carboxamides in a panel of human and murine tumor cells in culture. The tumor cell lines in this table are selected to represent a range of histological and growth phenotypes. Their characteristics are described below.

According to Table 3, the compounds of this invention are active at low concentrations against human breast carcinoma cells in culture, including cell lines resistant to the important clinical agents doxorubicin and mitoxantrone. They show little or no cross-resistance in these cell lines. Furthermore, they are active at comparable low concentrations against colon cancer, lung cancer, and ovarian cancer cell lines.

noma originally derived from a pleural effusion in a female with advanced metastatic breast cancer. (Soule, et al., *J Natl Cancer Inst* 51:1409–1416, 1973.)

1.2 MCF-7/ADR: This multidrug-resistant MCF-7 cell line was developed by growth in medium containing serially increasing concentrations of the antitumor agent doxorubicin (Adriamycin®). (Cohen, et al., *Cancer Res* 46:4087–4090, 1986.) The resistance pattern is stable when the cells are grown in medium of doxorubicin and the cells are cross-resistant to numerous other natural product-based antitumor agents including vincristine, vinblastine, etoposide, and dactinomycin. The MCF-7 ADR line is 192-fold less sensitive to doxorubicin in vitro and is known to express the cell membrane efflux (resistance) pump, P-glycoprotein.

TABLE 3

Antitumor Activities of Aziridine-1-carboxamides in Human Solid Tumor Cell Lines

| | | $IC_{50}$ ($\mu$g/mL) | | | | | | |
|---|---|---|---|---|---|---|---|---|
| | | MCF-7 Breast | | | WiDr | A-549 | A-375 | OVCAR3 |
| AMP No. | Example No. | sens. | D40 | mitox. | colon | lung | melanoma | ovarian |
| 403 | 1 | 3.3 | 2.1 | 2.3 | | | 2.1 | 1.7 |
| 404 | 8 | 0.5 | 0.5 | 0.8 | 0.9 | 1.6 | 2.1 | 1.3 |
| 406 | 2 | 4.0 | 2.8 | 1.4 | 5.6 | 2.5 | 5.0 | 2.0 |
| 407 | 12 | | | | | | 2.0 | 0.6 |
| 410 | 4 | >10 | 31.8 | 20.1 | 30 | 33 | 69.9 | 31.1 |
| 412 | 6 | 1.5 | 1.2 | 0.7 | 1.1 | 1.5 | 2.2 | 1.0 |
| 413 | 5 | 2.5 | 1.7 | 1.9 | 0.4 | 1.9 | 6.7 | 5.9 |
| 414 | 3 | | | | | | 2.5 | 2.0 |
| 415 | 9 | 0.4 | 0.5 | 0.6 | 0.4 | 1.3 | 0.7 | 1.2 |
| 416 | 10 | 0.4 | 0.4 | 0.3 | 0.3 | 1.1 | 3.0 | 1.5 |
| 417 | 11 | | | | | | 0.9 | 1.5 |
| 419 | 14 | | | | | 1.5 | 2.0 | 1.5 |
| 420 | 7 | | | | | | 10 | 10 |
| 421 | 19 | | | | | | 2.3 | 1.9 |
| 422 | 17 | | | | | | 50 | 50 |
| 423 | 18 | | | | | | 1.0 | 1.4 |
| 424 | 15 | | | | | | >10 | >10 |
| 425 | 16 | | | | | | 1.8 | 2.23 |

Sens. = Sensitivity to doxorubicin
D 40 = 40-fold doxorubicin resistant
Mitox = Mitoxantrone resistant pb

Description of Cell Lines Used to Characterize Antitumor Activity of Imexon Analogs In Vitro 1.0 Human Breast Tumor Cell Lines 1.1 MCF-7 Breast Cancer: The parental (sensitive) MCF-7 breast cancer is an estrogen-dependent adenocarci- 1.3 MCF-7/D40 and MCF-7/MITOX cell lines were developed by chronic exposure in vitro to increasing concentrations of the DNA-intercalating antitumor agents doxorubicin and mitoxantrone, respectively. (Taylor, et al., *Br J Cancer* 63:923–929, 1991.) These resistant cell lines have similar growth characteristics to the parental MCF-7 cells, but exhibit a multidrug resistance phenotype. The MCF-7/D40 cells express the cell membrane efflux pump, P-glycoprotein and are over 40-fold resistant to doxorubicin, mitoxantrone and the vinca alkaloids, vinblastine and vincristine. In addition, MCF-7/DOX40 cells can be sensitized (resistance reversed) using the antiarrhythmic agent verapamil. The MCF-7/MITOX cells are similarly multidrug resistant (but do not express either P-glycoprotein or the MRP resistance protein) (Futscher, et al., *Biochem Pharmacol* 47(9):1601–1606, 1994), and resistance is not modulated (reversed) by verapamil. Furthermore, the MCF-7/MITOX cells are only partially resistant to doxorubicin, but are highly resistant to other natural products.

2.0 Human WiDr Colon Cancer Cell Lines 2.1 WiDr: The adenocarcinoma cell line WiDr was originally isolated by Noguchi, et al. from a primary colon tumor specimen from a patient with advanced colon carcinoma. (Noguchi, et al, In Vitro 35(6):401–407, 1979.) The WiDr MITOX cell line was developed for mitoxantrone resistance by growth in serially elevated concentration of mitoxantrone. (Wallace, et al., *Proc Am Assoc Cancer Res* 23:767, 1982.) It is P-glycoprotein negative and exhibits 21-fold resistance to mitoxantrone, 8-fold resistance to doxorubicin and only 2-fold resistance to vincristine. (Dalton, et al., *Cancer Res* 48:1882–1888, 1988.)

3.0 A-549 Human Lung Cancer is an adenocarcinoma type of non-small cell lung cancer (NSCLC). It was established by Girard, et al. from a fresh tumor specimen obtained from a 58 year-old male with advanced lung cancer. (Girard, et al., *J Natl Cancer Inst* 51(5):1417–1423, 1973.) It has 5.6% plating efficiency (colony formation) on agar-coated plates, 66 modal chromosome number and grows rapidly when injected subcutaneously, forming acinar pattern tumors in immunodeficient mice. (Girard, et al., *J Natl Cancer Inst* 51(5):1417–1423, 1973.) Like NSCLC in vivo, A-540 lung cancer cells are relatively resistant to most chemotherapy drugs in vitro but like MCF-7 and WiDr, is used to screen for new anticancer agents in the NCI in vitro screening planel. (Alley, et al., *Cancer Res* 48:589–601, 1988.)

4.0 The Human A-375 Malignant Melanoma Cell Line was also developed by Girard, et al. (Girard, et al., *J Natl Cancer Inst* 51(5):1417–1423, 1973) from a 54 year-old human female with advanced melanoma. The modal chromosome number is 67 and it has a low plating (colony forming) efficiency of 0.7% when grown on agar. These cells also form rapidly growing tumors when injected subcutaneously into immunodeficient athymic (nu/nu) mice. (Girard, et al., *J Natl Cancer Inst* 51(5):1417–1423, 1973.) These cells are also used in the NCI drug screening panel. (Skehan, et al., *J Natl Cancer Inst* 82:1107–1112, 1990.)

5.0 Human OVCAR-3 Ovarian Carcinoma was originally isolated by Hamilton, et al. Experimental model systems of ovarian cancer; applications to the design and evaluation of new treatment approaches. *Seminar in Onocology,* 11:285–298, 1984, from a patient with progressive adenocarcinoma of the ovary. This patient had relapsed after receiving a combination chemotherapy regimen containing cyclophosphamide, doxorubicin and cisplatin. The cells grow as a cobblestone-like monalayer on plastic, have several chromosomal abnormalities, and possess intracellular hormonal receptors for androgens and estrogens. The OVCAR-3 cell line is resistant in vitro to clinically relevant concentrations of doxorubicin, melphalan and cisplatin. It is also one of the standard human tumor cell lines used for screening new anticancer agents at the NCI. (Alley, et al., *Cancer Res* 48:589–601, 1988.)

6.0 Development and Characterization of an Imexon-Resistant Human 8226 Myeloma Cell Line The following unpublished studies were performed in vitro to develop and characterize a human myeloma cell line with resistance to imexon-induced cytotoxicity. The original (parental) 8226 cell line was developed by Matsuoka, et al. (Matsuoka, et al., *Proc Soc Exp Biol Med* 125:1246–1250, 1967). It is a lymphoblastoid cell line which stains for lambda light immunoglobulin production. It grows in vitro in suspension culture (non-adherent) and forms tumors when injected into SCID mice. (Skehan, et al., *J Natl Cancer Inst* 82:1107–1112, 1990.)

EXAMPLE 21

Selection of Imexon-Resistant Cells and Cell Growth Characteristics

One exciting feature of our novel compounds is, that they work on imexon-resistant cells. An imexon-resistant 8226 myeloma cell line was selected by continuously exposing cells to gradually increasing concentrations of imexon up to 3.25 mg/mL. This cell line has slightly longer cell doubling time than 8226 sensitive cells (24 vs 20 hours). The survival curves for 8226 imexon-resistant cells (8226/I-R) and 8226 sensitive cells (8226/S) in the presence of imexon are showed in FIG. 2 which provides dose response curves for imexon on 8226 myeloma cells. The dose response curve for imexon continuous exposure was determined using MTT assay. Each data point represents the mean of three experiments performed in 8 replicates.

Figure 2:
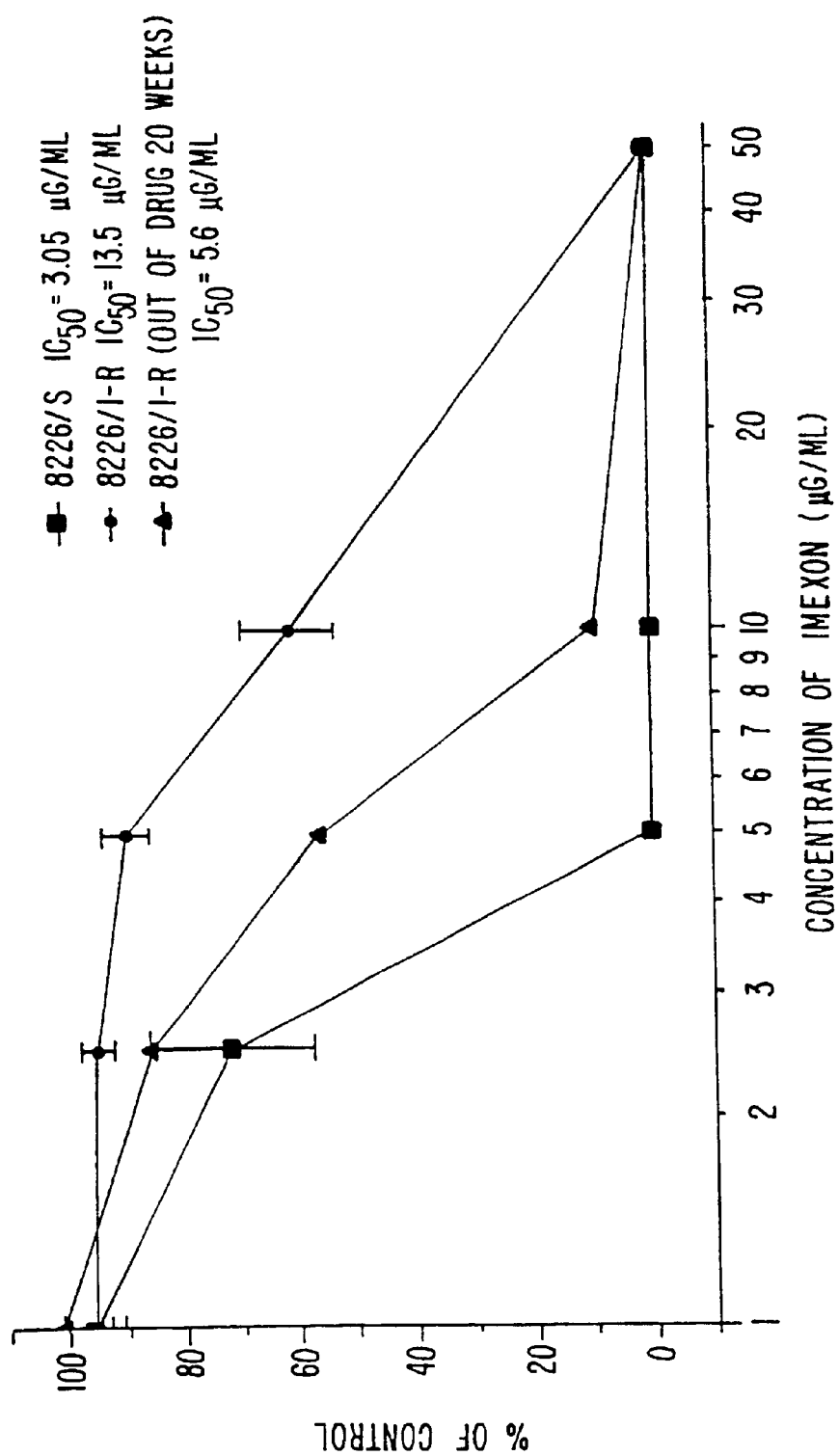
FIG. 2. Dose response curve for imexon on 8226 myeloma cells.

We compared $IC_{50}$ concentrations and there is a 4-fold resistance observed for the 8226/I-R cell line when the cells were continuously exposed to imexon for 5 days at 37° C. The degree of resistance was relatively unstable in the absence of the drug, with the resistant cells losing substantial resistance when maintained in imexon-free medium for 20 weeks (FIG. 2).

Cytogenetic Studies

Figure 3A:
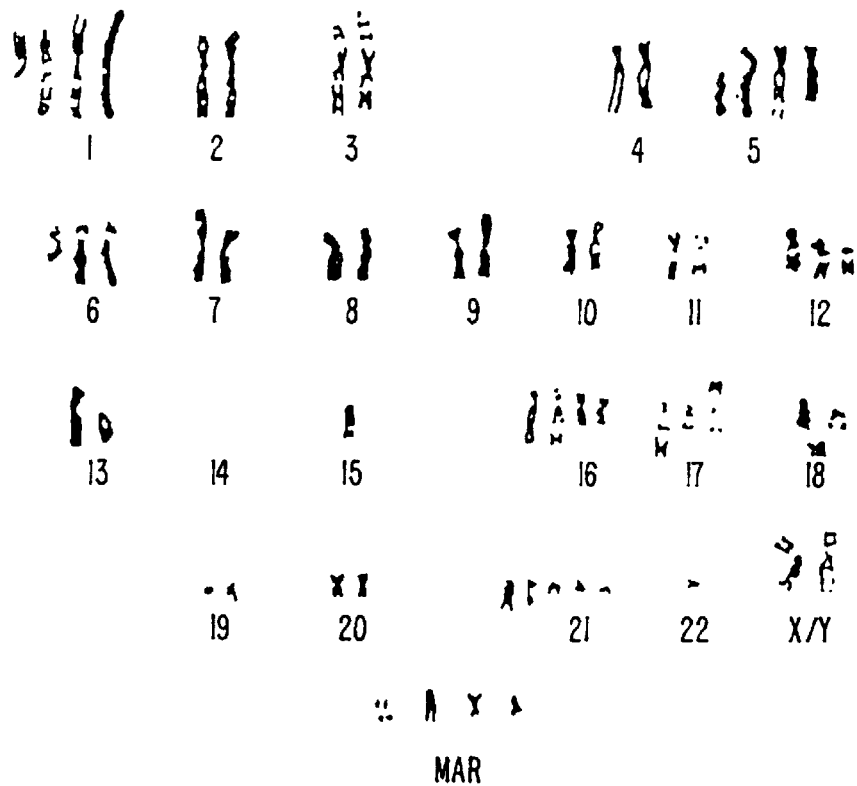
FIG. 3. G-banded karyotype of 8226 myeloma cells. A: 8226 sensitive cells with unidentifiable markers. B: 8226 imexon-resistant cells with unidentifiable markers.
Figure 3:
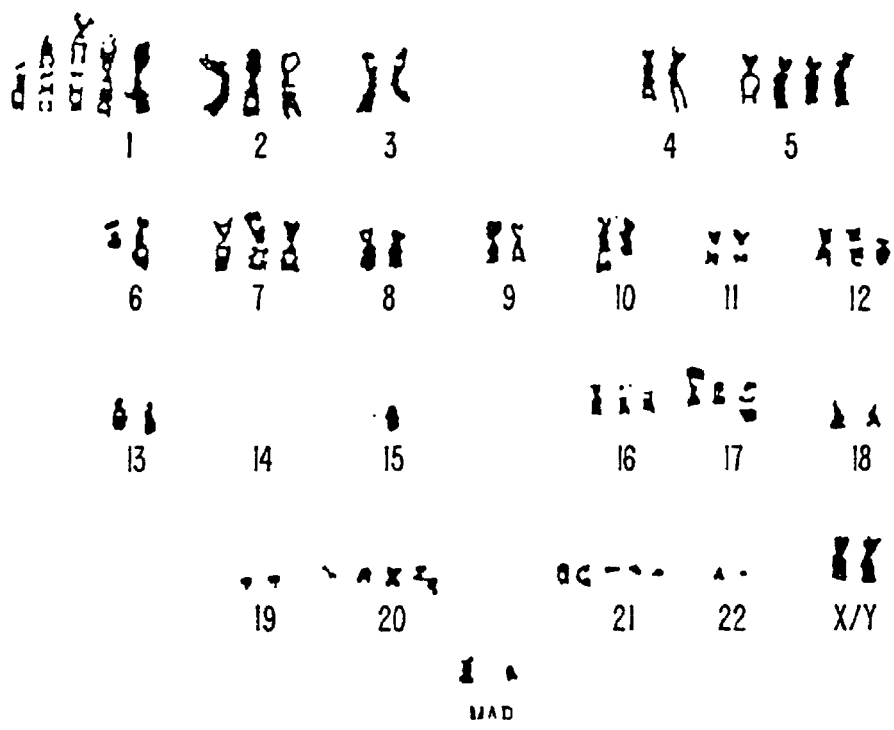
Figure 4:
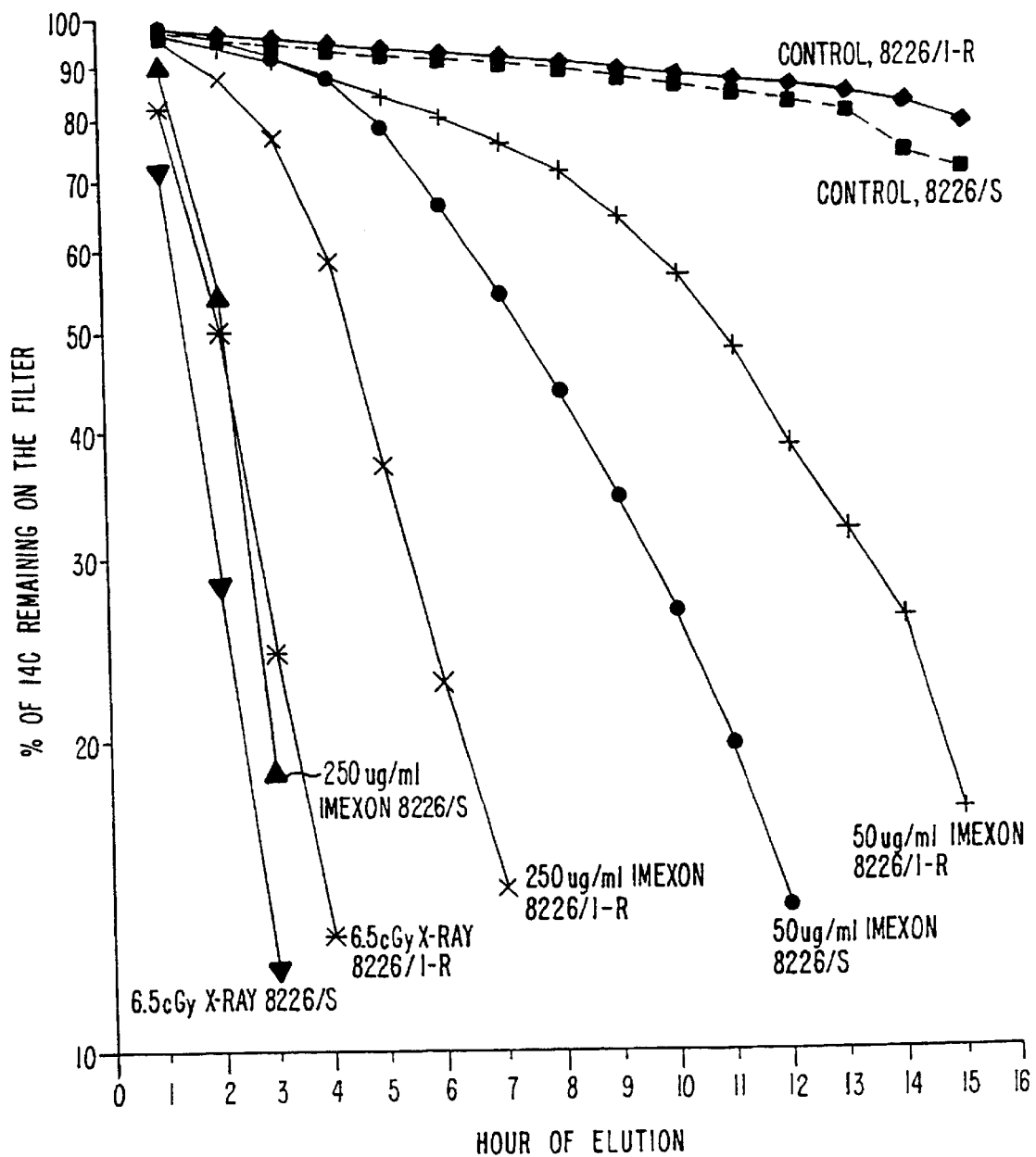
FIG. 4. Imexon induced single strand breaks in both 8226 imexon-sensitive and resistant cells (Imexon 50 mg/mL= 0.45 mM, 250 mg/mL=2.25 mM).

The range of chromosome counts was 48–79 in 8226/S and 51–62 for 8226/I-R with modal populations of 57–59 (59%) and 61 (40%). Both cell lines had 12 identifiable structural abnormalities, including dic(1;14), t(1;14) (p13;q32), add(3)(q29), del(5)(q32), der(5)t(5;6), der(7)t (3;7) add(9)(p24), del(11)(q24), del(12)(p11.2), add(16) (q24), der(17) t(11; 17) and 21 qhsr. The imexon-resistant cell line had two additional structure rearrangements that are del(1)(p22) and add(6)(q13). The guanine-banded karyotype of 8226/S and 8226/I-R cells was shown in FIG. 3. Since there was a rearrangement at der(7)t(3,7) which was a characteristic of 8226/V cells (a cell line developed for resistance to verapamil), the 8226/S cells were actually 8226/V cells.

Cross-Resistance Study

The cross-resistance profile of imexon-resistant cells measured by MTT assay is shown in Table 4. The 8226 imexon-resistant cells showed partial cross-resistance to the platinum-type DNA intrastrand cross linkers, cisplatin and carboplatin. There is also partial resistance to the bioreductive aziridine-based alkylator mitomycin C. However, this imexon-resistant cell line remains sensitive to natural products, including doxorubicin, vincristine, and bleomycin and X-radiation.

TABLE 4

Cross-Resistance Patterns of Imexon-Resistant 8226 Human Myeloma Cells to Various Antitumor Agents.

| | $IC_{50}$(M) | | |
|---|---|---|---|
| Agent | 8226/S | 8226/I-R | Fold Resistance[a] |
| Imexon | $2.7 \times 10^{-5}$ | $1.2 \times 10^{-4}$ | 4.44 |
| Nitrogen Mustard | $6.6 \times 10^{-6}$ | $6.0 \times 10^{-6}$ | 0.91 |
| Melphalan | $6.2 \times 10^{-8}$ | $5.3 \times 10^{-6}$ | 0.81 |
| Cisplatin | $1.1 \times 10^{-6}$ | $2.0 \times 10^{-6}$ | 1.85 |
| Carboplatin | $9.7 \times 10^{-6}$ | $1.6 \times 10^{-5}$ | 1.65 |
| Mitomycin C | $6.6 \times 10^{-8}$ | $9.9 \times 10^{-8}$ | 1.50 |
| Vincristine | $2.8 \times 10^{-9}$ | $2.4 \times 10^{-9}$ | 0.88 |
| Doxorubicin | $4.3 \times 10^{-10}$ | $3.2 \times 10^{-10}$ | 0.79 |
| Bleomycin[a] | 7.0 µg/ml | 7.8 µg/ml | 1.11 |
| X-Ray Radiation[b] | 4.75 | 4.6 | 0.97 |

[a]$IC_{50}$ resistant cells/$IC_{50}$ sensitive cells.
[b]cGy.

$IC_{50}$ was measured by MTT assay. $IC_{50}$ refer to the concentration by drug that results in 50% growth inhibition. A minimum of 2 assays were performed for each drug following 250 mg/mL imexon is equivalent to 6.5 cGy radiation in sensitive cells.

We then composed the $IC_{50}$ of the novel cyanoaziridines against the 8226/S- and 8226/I-R lines. Of the 20 compounds tested, 11 were as active against the imexon-resistant as imexon-sensitive lines showing a degree of resistance of 1.3 or less ($IC_{50}$ I-R/$IC_{50}$S), (Table 5).

TABLE 5

Comparison of Imexon Analog Activity in Parental (Sensitive) and Imexon-Resistant Human 8226 Myeloma cells.

| | | $IC_{50}$ (µg/mL) | | Fold Resistance |
|---|---|---|---|---|
| AMP No. | Example No. | Sensitive | Resistant | of $IC_{50}$ R/$IC_{50}$'s |
| Imexon | | 1.0 | 8.5 | 4.5 |
| 403 | 1 | 3.3 | 3.3 | 1.0 |
| 404 | 8 | 1.0 | 1.5 | 1.5 |
| 406 | 2 | 3.1 | 3.6 | 1.2 |
| 407 | 12 | 1.2 | 2.4 | 2.0 |
| 408 | 13 | 0.27 | 0.68 | 2.5 |
| 409 | | 32 | 48 | 1.5 |
| imexon intermediate | | | | |
| 410 | 4 | 20 | 36 | 1.8 |
| 412 | 6 | 1.8 | 2.2 | 1.2 |
| 413 | 5 | 7.0 | 19 | 1.2 |
| 414 | 3 | 2.8 | 2.8 | 1.0 |
| 415 | 9 | 1.0 | 1.2 | 1.2 |
| 416 | 10 | 2.1 | 2.0 | 0.95 |
| 417 | 11 | 2.1 | 2.0 | 0.95 |
| 419 | 14 | ND* | ND* | — |
| 420 | 7 | 5.0 | 6.0 | 1.2 |
| 421 | 19 | 2.2 | 2.8 | 1.3 |
| 422 | 17 | >100 | <100 | — |
| 423 | 18 | 1.0 | 2.1 | 2.1 |
| 424 | 15 | >100 | >100 | — |
| 425 | 16 | 1.98 | 2.2 | 1.1 |

*ND = No data.

Example 22

Comparison of Imexon and Analog Series in the Imexon-Resistant 8226 Myeloma Cells in vitro Using the colorimetric microculture tetrazolium (MTT) assay, imexon and 25-related analogs were studied for tumor growth inhibition in vitro. Imexon-induced DNA single strand breaks were assessed by alkaline elution. Cells were exposed to imexon for 1 hour prior to start of experiment. The fraction of $^{14}$C-labeled DNA retained on the filter is plotted against the time of elution. The cells included parental 8226 myeloma cells and the 8226 imexon-resistant cells exposed to drug (imexon or analog) continuously for 10 days at 37° C. At the end of the exposure period, the cells were analyzed for viability using the formazan-forming tetrazolium dye (MTT) assay. For a given dose of imexon, there are fewer strand breaks in imexon-resistant cells than in sensitive cells (statistical comparison the time at which 20% of $^{14}$C remaining on the filter, p<0.05, n 32 2).

The results show that imexon induces concentration-dependent single-stranded breaks in tumor cell DNA at drug concentrations which are within the range which inhibits myeloma tumor cell growth in vitro. These strand breaks are noted by an enhanced rate of $^{14}$C-DNA elution through the filters after a one-hour exposure to imexon (10–500 µg/mL) at 30° C. At high imexon concentrations of $\geq$100 µg/mL, over 75% of the radiolabeled DNA is eluted through the filters over the test period. By comparison, control cell DNA is highly retained (>95%) on the filter over the same 24-hour elution period. These results suggest that imexon directly or indirectly damages tumor cell DNA at drug levels which are active in vitro.

In addition, the imexon analogs have also been tested in a multidrug-resistant (MDR) mouse L-1210 leukemia cell line.

Murine L-1210 Leukemia Cells were first described by Law, et al. from a female DBA/2 mouse exposed to topical methylcholanthrene. (Law, et al., *J Natl Cancer Inst* 10:179–192, 1949.) The cells represent a lymphocytic lineage and are highly tumorigenic in syngeneic DBA/2 mice, producing lethality typically 10–14 days after inoculation. This cell line has been used extensively to characterize the antitumor activity of chemotherapeutic agents. (Goldin, et al., Cancer Res (Cancer Chemotherapy Screening Data IX) 21:27–92, 1961.) The L-1210 cells have a model 40–41 chromosomes and a very high plating efficiency in suspension cultures in vitro.

L-1210 MDR Cells represent a multidrug-resistant cell line developed for resistance to the alkylating agent mitomycin C. (Dorr, et al., *Biochem Pharmacol* 36(19) :3115–3120, 1987.) This cell line has the same general growth characteristics of the parental line, but is cross-resistant to numerous natural-product based anticancer agents. This includes anthracyclines such as doxorubicin (Adriamycin®) and vinca alkaloids such as vincristine or vinblastine. The L-1210 MDR cells express elevated levels of membranal P-glycoprotein and resistance can be reversed using modulators such as verapamil.

The findings are similar to those in MDR myeloma in that most of the analogs exhibit no cross-resistance in a cell line which has upregulated p-glycoprotein. The results are provided in Table 6.

TABLE 6

Antitumor Activity of Aziridine-1 Carboxamides in Sensitive and Multidrug-Resistant (MDR) Mouse L-1210 Leukemia Cells in vitro.

| | | $IC_{50}$ (µg/mL) | | Fold Resistance of |
|---|---|---|---|---|
| AMP No. | Example No. | Sensitive(s) | MDR | $IC_{50}$'s (MDR/S) |
| 403 | 1 | 1.1 | 2.7 | 2.5 |
| 404 | 8 | 0.2 | 2.1 | 10.5 |

TABLE 6-continued

Antitumor Activity of Aziridine-1 Carboxamides in Sensitive and
Multidrug-Resistant (MDR) Mouse L-1210 Leukemia Cells in vitro.

| AMP No. | Example No. | IC$_{50}$ (μg/mL) Sensitive(s) | MDR | Fold Resistance of IC$_{50}$'s (MDR/S) |
|---|---|---|---|---|
| 406 | 2 | 2.0 | 2.0 | 1.0 |
| 407 | 12 | 52.3 | 8.4 | 0.16 |
| 408 | 13 | 0.7 | 1.9 | 2.7 |
| 409 | 32 | >10.0 | >10.0 | |
| 410 | 4 | 22.0 | 30.7 | 1.4 |
| 412 | 6 | 0.8 | 2.1 | 2.6 |
| 413 | 5 | 1.4 | 3.1 | 2.2 |
| 414 | 3 | 2.0 | 2.0 | 1.0 |
| 415 | 9 | 1.5 | 1.2 | 0.8 |
| 416 | 10 | 2.0 | 1.8 | 0.9 |
| 417 | 11 | 0.6 | 0.6 | 1.0 |
| 419 | 14 | 2.5 | 3.0 | 1.2 |
| 420 | 7 | 2.5 | 2.5 | 1.0 |
| 421 | 19 | 2.3 | 2.1 | 0.9 |
| 422 | 17 | >10 | >10 | 1.0 |
| 423 | 18 | 1.7 | 0.64 | 0.4 |
| 424 | 15 | >10 | >10 | 1.0 |
| 425 | 16 | 2.2 | 1.8 | 0.8 |

*Drug continuously present for 8 days; IC$_{50}$ measured by MTT dye reduction assay.

Significance

These results show that (1) analogs with enhanced potency (>40% decrease in IC$_{50}$) against myeloma cell growth can be identified (Nos. 407, 415, 423 and especially, 408); (2) there is a lack of significant (>50% IC$_{50}$ change) cross-resistance with imexon for many analogs (Nos. 403, 404, 412, 414, 415, 416, 417, 419, 420, 421 and 425); and conversely (3) some analogs have no antitumor effects even at high concentrations in the parental and imexon-resistant myeloma cells (Analog Nos. 422 and 424); and finally, (4) analogs with roughly equal potency to imexon and no significant cross resistance have been identified (Analog Nos. 412, 415, 416, 417 and 425). These results suggest that improved antitumor efficacy may be achieved with selected analogs of imexon.

Refractory Solid Tumors

In the in vitro screening panel, a number of analogs showed roughly equipotent sensitivity across the 12 cell line panel. For several analogs tumor cell sensitivity increased in a few of the non-hematologic (or solid) tumor cell lines. This was the case for AMP 404, 415 and 416 in all 3 MCF-7 breast cancer cell lines and in the parental WiDr colon cancer cell line. Importantly, this analog has already demonstrated antitumor activity in multidrug-resistant 8226 myeloma cells growing in SCID mice. The consistent observation of maintained potency in cell lines selected for multidrug resistance to natural products further suggests that the analogs could be used in salvage therapy regimens for solid tumor patients who relapse or fail to respond after initial existing chemotherapy agents. Of note, this was the type of official indication recently given for the FDA approval of taxotere in patients with advanced breast cancer who relapse after receiving therapy with regimens containing the natural product DNA intercalator, doxorubicin. Based on the in vitro database, the imexon analogs should have clinical applicability in advanced breast cancer, lung cancer and possibly in colon cancer.

The prior preliminary clinical studies with imexon buttress the notion that imexon analogs may be useful in drug-refractory solid tumors. In an early report of European Phase I studies with imexon in cancer patients with a variety of advanced solid tumors, imexon induced objective (measurable) responses in 1/7 evaluable patients each with lung cancer, melanoma and breast cancer. (Mickshe, et al., *Cancer Treat Symp* 1:27–35, 1985.) Notably, the responses in lung cancer and melanoma involved complete disappearance of all measurable disease for 33 and 42 months, respectively. Furthermore, there were 8 additional patients with advanced tumors who experienced disease stabilization with durations ranging from 4–24 months. This is remarkable since ail of these patients were heavily pretreated with drugs and/or radiotherapy, and by definition, in Phase I study, the optimal drug dose is not being used. A more recent report from this group has confirmed these initial observations of imexon activity for imexon doses of 1,200 mg/4 weeks up to 11,000 mg over a 24-month period. (Sagaster, et al., *J Natl Cancer Inst* 87(12):935–936, 1995.) In the one patient with metastatic non-small cell lung cancer (NSCLC), a complete remission has been documented for over 14 years, and stable disease was achieved in 6 patients: one with NSCLC, four with breast cancer and one with liver cancer. (Sagaster, et al., *J Natl Cancer Inst* 87(12):935–936, 1995.) The only consistent toxic effect noted in these patients was mild, transient nausea (13%) and vomiting (23%). Thus, imexon appears to have activity in drug-refractory solid tumors at doses which produce only mild short-term toxic effects.

Example 23

Clinical Applications

A. Treating Myeloma

The following protocol is appropriate for Analogue 404 to treat human myeloma which is a B-lymphocyte-derived bone marrow disease. Analogue 404 is formulated in a sterile, isotonic standard saline or dextrose buffer at pH 7.0 at a concentration of 500 μg/ml. The solution is administered intravenously to a patient with hematologic cancer at a rate of 5,000 μg/minute duration via an intravenous route. The total dose is 3.5 g/m$^2$ given 500 mg/m$^2$/day×7 days as a continuous IV infusion.

Anti-tumor effects can be measured using the level of circulating myeloma M protein and bone marrow biopsy. Other therapeutic effects which are observed are an improvement of anemia, a correction of hypercalcemia and a diminution of bone pain. Treatment is repeated every two to four weeks until the patient responds in a suitable manner.

B. Treatment of Melanoma

Using the treatment protocol for example 23, but substituting a patient suffering from melanoma. Patient metastases are monitored every 8–12 weeks by x-rays and scans.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of the formula 1:

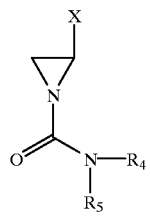

wherein X is CN;
wherein $R_4$ is hydrogen or lower alkyl of 1–4 carbons; and, wherein $R_5$ is an alkyl of 1–8 carbons, lower cycloalkyl of 4–7 carbons, alkenyl of 1–6 carbons, an aryl of 4–10 carbons, a substituted aryl of 4–12 carbons, a heterocyclic group of 4–16 members, with the proviso that when X is CN, and $R_4$ is hydrogen, then $R_5$ is not $CH_3$, $C_6H_5$, or, p-nitrophenyl.

2. A compound of claim 1:
wherein X is CN;
wherein $R_4$ is hydrogen or lower alkyl of 1–4 carbons; and, wherein $R_5$ is an alkyl of 1–8 carbons, lower cycloalkyl of 4–7 carbons, alkenyl of 3–6 carbons, an aryl of 4–10 carbons, a substituted aryl of 4–12 carbons having 1–2 substitutents wherein the substituents are independently selected from the group consisting of lower alkyl of 1–4 carbons, nitro, halo substituted lower alkyls of 1–4 carbons, a lower alkyl substituted acyloxy of 1–5 carbons, a lower alkyl substituted acyl of 1–5 carbons, a heterocyclic group of 4–16 members.

3. A compound of claim 1 wherein X is CN.

4. A compound of claim 2 wherein
$R_4$ is hydrogen; and
$R_5$ is a straight chain alkyl of 1 to 8 carbons, an unsubstituted aryl, a mono-substituted or disubstituted aryl wherein the aryl is independently substituted with halo, lower alkyl, halo substituted lower alkyl, acyl or lower alkyl-substituted acyloxy.

5. A compound of claim 2 wherein $R_4$ is hydrogen; and $R_5$ is a heterocyclic group or a substituted aryl.

6. A compound of claim 2 wherein $R_4$ is hydrogen; and $R_5$ is a pyridyl, a substituted phenyl or a naphthyl.

7. A method of treating cancer, wherein the cancer is selected from the group comprising multiple myeloma, a β-lymphocyte plasmacytoma, advanced stage ovarian epithelial cell cancer, metastatic melanoma, leukemias of lymphoid and nonlymphoid origin, metastatic colon cancer, breast cancers and metastatic lung cancers, by administering to a patient in need of treatment an a unit dose of a compound of formula 1 in claim 1:
wherein X is CN;
wherein $R_4$ is hydrogen or lower alkyl of 1–4 carbons;
wherein $R_5$ is an alkyl of 1–8 carbons, lower cycloalkyl of 4–7 carbons, alkenyl of 1–6 carbons, an aryl of 4–10 carbons, a substituted aryl of 4–12 carbons, a heterocyclic group of 4–16 members; and,
wherein said unit dose is effective to reduce at least one of the symptoms of the cancer.

8. A method of claim 7 wherein in the said compound X is cyano.

9. A method claim 7 wherein the unit dose of the said compound is 0.25 to 2 grams.

10. A method of claim 7 wherein the unit dose of the said compound is administered via a parenteral route.

11. A method of claim 7 wherein the cancer is selected from the group comprising multiple myeloma, a β-lymphocyte plasmacytoma, advanced stage ovarian epithelial cell cancer, metastatic melanoma, leukemias of lymphoid and nonlymphoid origin, metastatic colon cancer, breast cancers and metastatic lung cancers.

12. A pharmaceutical composition comprising a unit dose of a compound of claim 1 in a sterile aqueous solution, or in a water-miscible formulation.

13. A pharmaceutical composition of claim 12 which further comprises pharmaceutically acceptable excipients.

* * * * *